US011248252B2

(12) United States Patent
Zhu et al.

(10) Patent No.: US 11,248,252 B2
(45) Date of Patent: Feb. 15, 2022

(54) TREATMENT AND DIAGNOSIS OF IMMUNE DISORDERS

(71) Applicants: Zhenglun Zhu, Newton, MA (US); Hong Gao, Downingtown (PA)

(72) Inventors: Zhenglun Zhu, Newton, MA (US); Hong Gao, Downingtown (PA)

( * ) Notice: Subject to any disclaimer, the term of this patent is extended or adjusted under 35 U.S.C. 154(b) by 468 days.

(21) Appl. No.: 16/011,182

(22) Filed: Jun. 18, 2018

(65) Prior Publication Data

US 2018/0282785 A1 Oct. 4, 2018

Related U.S. Application Data

(60) Continuation of application No. 14/294,565, filed on Jun. 3, 2014, now abandoned, which is a division of application No. 13/382,641, filed as application No. PCT/US2010/042126 on Jul. 15, 2010, now Pat. No. 8,741,865.

(60) Provisional application No. 61/225,852, filed on Jul. 15, 2009.

(51) Int. Cl.
| | |
|---|---|
| *C12Q 1/68* | (2018.01) |
| *A61K 31/7105* | (2006.01) |
| *C12N 15/113* | (2010.01) |
| *C12Q 1/6883* | (2018.01) |

(52) U.S. Cl.
CPC ............ *C12Q 1/68* (2013.01); *A61K 31/7105* (2013.01); *C12N 15/113* (2013.01); *C12Q 1/6883* (2013.01); *C12N 2310/14* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 5,583,153 | A | 12/1996 | Brahn |
| 7,745,391 | B2 * | 6/2010 | Mintz ..................... A61P 31/00 514/19.3 |
| 2004/0223952 | A1 | 11/2004 | Have-Opbroek et al. |
| 2006/0247193 | A1 | 11/2006 | Taira et al. |
| 2007/0161031 | A1 * | 7/2007 | Trinklein ............ C12Q 1/6897 435/6.11 |
| 2007/0248535 | A1 | 10/2007 | Buttyan et al. |
| 2008/0032927 | A1 | 2/2008 | Zhu et al. |

FOREIGN PATENT DOCUMENTS

| | | |
|---|---|---|
| EP | 2454372 | 5/2012 |
| WO | WO-2004/076622 A2 | 9/2004 |
| WO | WO-2007/051077 A2 | 5/2007 |
| WO | WO-2007/078599 A2 | 7/2007 |
| WO | WO-2007/101063 A2 | 9/2007 |

OTHER PUBLICATIONS

Pociot et al. (Scand J Immunol, 1993, 38:491-495) (Year: 1993).*
Gao et al "W1966 Hom-1 Inhibits Tumor Growth in Both P53 Sufficient and Deficient Colon Cancer Cells" Gastroenterology vol. 134, p. A-744, 2008.
Moreau-Aubry et al "A Processed Pseudogene Codes for a New Antigen Recognized by a CD8+ T Cell Clone on Melanoma". The Journal of Experimental Medicine, The Rockefeller University Press; May 1, 2000; pp. 1617-1623; vol. 191, No. 9.
Arce et al "Diversity of LEF/TCF Action in Development and Disease" Oncogene vol. 25, pp. 7492-7504, 2006.
Arseni et al "The VENT-Like Homeobox Gene Ventx2 is Expressed in Human Hematopoietic Progenitor Cells and Promotes Human Myeloid Development in vitro and in vivo" Annals of Hematology vol. 87, p. S15, 2008.
Arseni et al "The Vent-Like Homeobox Gene VENTX2 is Expressed in Human Hematopoietic Progenitor Cells and Promotes Human Myeloid Development in vitro and in vivo" Blood vol. 110, pp. 383A-384A, 2007.
Arseni et al "VENTX2—A Vent-Like Homeobox Gene—Is a Novel Candidate for a Hematopoietic Regulatory Protein" Experimental Hematology vol. 35, p. 45, 2007.
Cong et al "Requirement for a Nuclear Function of β-Catenin in Wnt Signaling" Molecular and Cellular Biology vol. 23, pp. 8462-8470, 2003.
GeneBank Accession No. BC108916, *Homo sapiens* VENT Homeobox Homolog (*Xenopus laevis*), mRNA (cDNA Clone MGC:119911 Image: W015553), Complete CDS. 2006.
Maye et al "Multiple Mechanisms for Wnt11-Mediated Repression of the Canonical Wnt Signaling Pathway" The Journal of Biological Chemistry vol. 279, pp. 24659-24665, 2004.
Shulewitz et al "Repressor Roles for TCF-4 and Sfrp1 in Wnt Signaling in Breast Cancer" Oncogene vol. 25, pp. 4361-4369, 2006.

* cited by examiner

*Primary Examiner* — Stephanie K Mummert
(74) *Attorney, Agent, or Firm* — Cesari & McKenna, LLP

(57) ABSTRACT

Disclosed are composition and methods for treating immune disorders. Also disclosed are diagnosis methods and prognosis methods.

9 Claims, 6 Drawing Sheets
Specification includes a Sequence Listing.

Figure 1A

```
Xom  176  RLRTAFTSDQISTLEKTFQKHRYLGASERQKLAAKLQLSEVQIKTWFQNRRMKYKREIQD  235
          R+RTAFT  +Q+  TLE   FQ H+YL     ER++LA  ++QLSEVQIKTWF QNRRMK+KR++QD
Hom-1  93 RVRTAFTMEQVRTLEGVFQHHQYLSPLERKRLAREMQLSEVQIKTWFQNRRMKHKRQMQD  152
```

Figure 1B

```
                                                                          Section 1
              (1)    1        10        20        30        40        55
Homo Sapiens  (1)    MRLSSSPPRGPQQLSSFGSVDWLSQSSCSGPTHTPRPADFSLGSLPGPGQTSGAR
Chimpanzee    (1)    MRLSSSPPRGPQQLSSFGSVDWLSQSSCSGPTHTPRPADFSLGSLPGPGQTSGAR
rhesus monkey (1)    MRLSSSPPRGQQPSSFGSVDWLSQSSCGLTPFRPADVSPGSLPGPGQISGAR
Consensus     (1)    MRLSSSPPRG  QQLSSFGSVDWLSQSSCSGPTHTPRPADFSLGSLPGPGQTSGAR
                                                                          Section 2
             (56)   56        70        80        90       100       110
Homo Sapiens (56)   EPPQAVSIKEAAGSSNLPAPERTMAGLSKEPNTLRAPRVRTAFTMEQVRTLEGVF
Chimpanzee   (56)   EPPQAVSIKEAARSSNLPAPERTVAGLSKEPNTLRVPRVRTAFTMEQVRTLEGVF
rhesus monkey(56)   EPPQALSIKEAVRRSALPSPQPSMPGLSKEPNTLRGPRVRTAFTTEQVRTLEGVF
Consensus    (56)   EPPQAVSIKEAARSSNLPAPERTMAGLSKEPNTLRAPRVRTAFTMEQVRTLEGVF
                                                                          Section 3
            (111)  111       120       130       140       150       165
Homo Sapiens(111)  QHHQYLSPLERKRLAREMQLSEVQIKTWFQNRRMKHKRQMQDPQLHSPFSGSLHA
Chimpanzee  (111)  QHHQYLSPLERKRLAREMQLSEVQIKTWFQNRRMKHKRQMQDPQLHSPFSGSLPA
rhesus monkey(111) QHHQYLSPLERKRLAREMQLSEVQIKTWFQNRRMKHKRQMQEVPPNSPFLGSLHV
Consensus   (111)  QHHQYLSPLERKRLAREMQLSEVQIKTWFQNRRMKHKRQMQDPQLHSPFSGSLHA
                                                                          Section 4
            (166)  166       180       190       200       210       220
Homo Sapiens(166)  PPAFYSTSSGLANGLQLLCPWAPLSGPQALMLPPGSFWGLCQVAQEALASAGASC
Chimpanzee  (166)  PPAFYSPSSGLANGLQLLCPWAPLSGPQALMLPPGSFWGLCQVAQEALASVGASC
rhesus monkey(166) PPAFHSPSSGLANGLQLLCPWAPLPGPQALMLPPGSFWGLCQVEQEALASTGASC
Consensus   (166)  PPAFYSPSSGLANGLQLLCPWAPLSGPQALMLPPGSFWGLCQVAQEALAS GASC
                                                                          Section 5
            (221)  221       230       240       250       260
Homo Sapiens(221)  CGQPLASHPPTPGR--PSLGPALSTGPRGLCAMPQTGDAF
Chimpanzee  (221)  CGQPLASHPPTPGR--PTLGPALSTGPRGLCAMFQTGDAF
rhesus monkey(221) CRQPLAHHPPTIGSGLPAPGPALSTGPWGLCALPETGDAF
Consensus   (221)  CGQPLASHPPTPGR  PSLGPALSTGPRGLCAMPQTGDAF
```

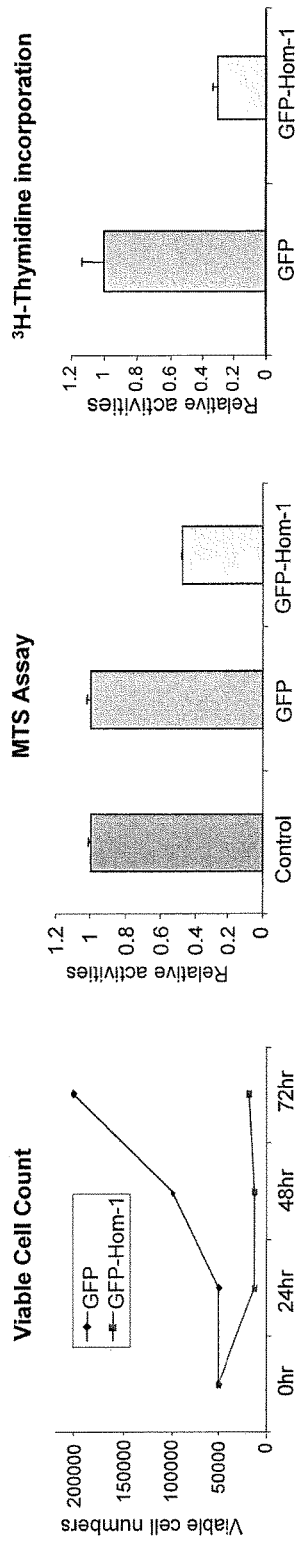
Figure 3A
Figure 3B
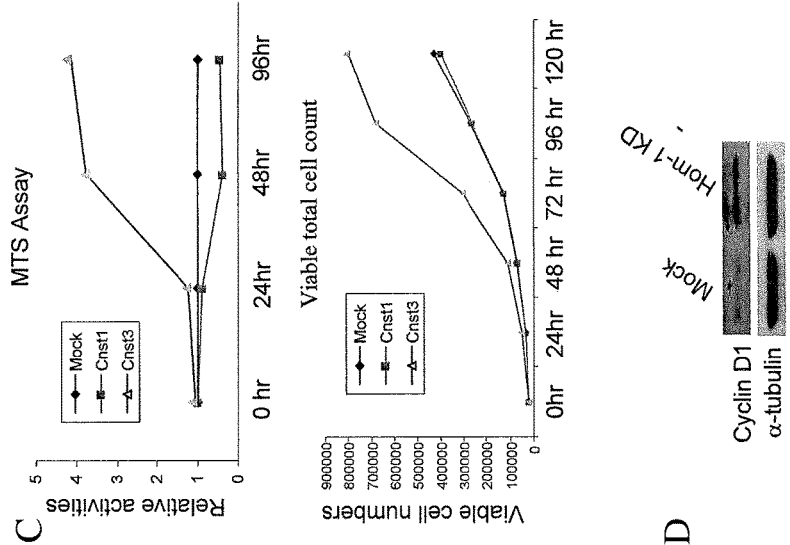
Figure 3C
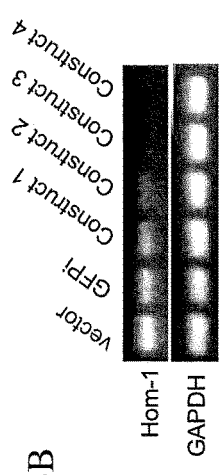
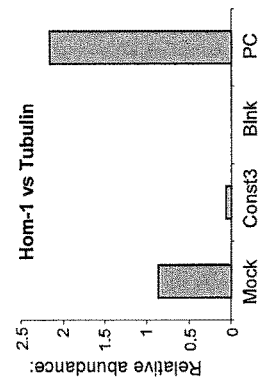
Figure 3D

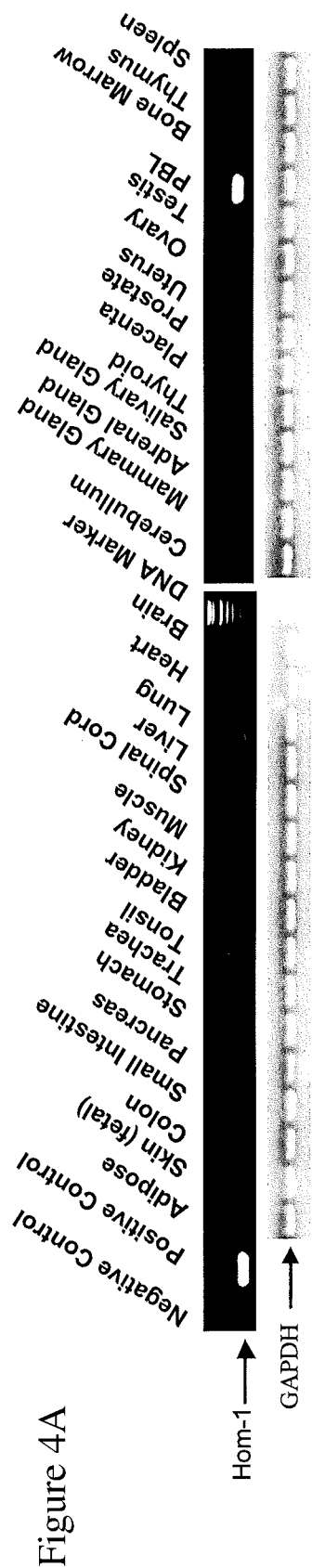
Figure 4A
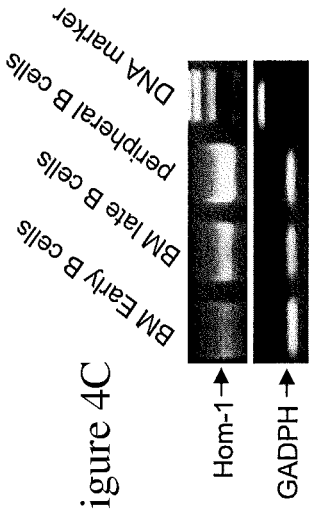
Figure 4B
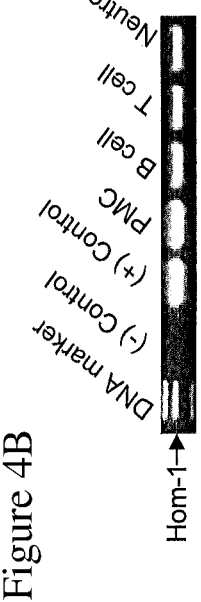
Figure 4C
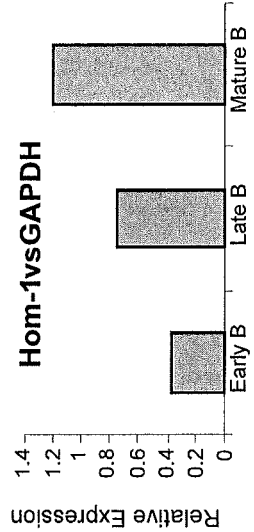
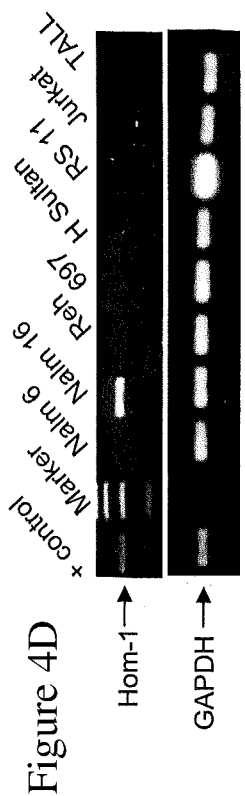
Figure 4D

SEQUENCE LISTING

```
<160> NUMBER OF SEQ ID NOS: 21

<210> SEQ ID NO 1
<211> LENGTH: 258
<212> TYPE: PRT
<213> ORGANISM: Homo sapiens

<400> SEQUENCE: 1

Met Arg Leu Ser Ser Ser Pro Pro Arg Gly Pro Gln Gln Leu Ser Ser
1               5                   10                  15

Phe Gly Ser Val Asp Trp Leu Ser Gln Ser Ser Cys Ser Gly Pro Thr
            20                  25                  30

His Thr Pro Arg Pro Ala Asp Phe Ser Leu Gly Ser Leu Pro Gly Pro
        35                  40                  45

Gly Gln Thr Ser Gly Ala Arg Glu Pro Pro Gln Ala Val Ser Ile Lys
    50                  55                  60

Glu Ala Ala Gly Ser Ser Asn Leu Pro Ala Pro Glu Arg Thr Met Ala
65                  70                  75                  80
```

```
Gly Leu Ser Lys Glu Pro Asn Thr Leu Arg Ala Pro Arg Val Arg Thr
             85                  90                  95
Ala Phe Thr Met Glu Gln Val Arg Thr Leu Glu Gly Val Phe Gln His
            100                 105                 110
His Gln Tyr Leu Ser Pro Leu Glu Arg Lys Arg Leu Ala Arg Glu Met
        115                 120                 125
Gln Leu Ser Glu Val Gln Ile Lys Thr Trp Phe Gln Asn Arg Arg Met
    130                 135                 140
Lys His Lys Arg Gln Met Gln Asp Pro Gln Leu His Ser Pro Phe Ser
145                 150                 155                 160
Gly Ser Leu His Ala Pro Pro Ala Phe Tyr Ser Thr Ser Ser Gly Leu
                165                 170                 175
Ala Asn Gly Leu Gln Leu Leu Cys Pro Trp Ala Pro Leu Ser Gly Pro
            180                 185                 190
Gln Ala Leu Met Leu Pro Pro Gly Ser Phe Trp Gly Leu Cys Gln Val
        195                 200                 205
Ala Gln Glu Ala Leu Ala Ser Ala Gly Ala Ser Cys Cys Gly Gln Pro
    210                 215                 220
Leu Ala Ser His Pro Pro Thr Pro Gly Arg Pro Ser Leu Gly Pro Ala
225                 230                 235                 240
Leu Ser Thr Gly Pro Arg Gly Leu Cys Ala Met Pro Gln Thr Gly Asp
                245                 250                 255
Ala Phe

<210> SEQ ID NO 2
<211> LENGTH: 777
<212> TYPE: DNA
<213> ORGANISM: Homo sapiens

<400> SEQUENCE: 2
atgcgcctct cctcctcccc acctcgtggc ccgcagcagc tctccagctt tggctccgtg      60
gactggctct cccagagcag ctgctcaggg ccgacccaca cccccaggcc tgccgacttc     120
tccctgggga gcctccctgg cccaggccag acatccggcg cccggagccc cctcaggcc     180 gtcagcatca aggaggccgc cggg tcctca aatctgcctg cgccggagag gaccatggcc     240
gggttgagta aggagccaaa taccttgcgg gccccccgtg tccgcacagc cttcaccatg     300
gagcaggtcc gcaccttgga gggcgtcttc cagcaccacc agtacctgag ccctctggag     360
cggaagaggc tggccaggga gatgcagctc tcagaggtcc agataaaaac ctggtttcag     420
aatcgccgca tgaaacacaa acggcaaatg caggaccccc agctgcacag ccccttctcg     480
ggtctctccc atgcgccccc agctttctac tcaacgtctt ctggccttgc caatggcctg     540
cagctgctgt gccttgggc accctgtcc gggcccagg ctctgatgct gccccctggc     600
tccttctggg gtctctgcca agtggcacaa gaggcctgg catctgcggg agcttcctgc     660
tgcgggcagc ctctggcgtc ccacccccct accccaggcc ggccttcgct gggaccagcc     720
ctgtccacgg ggccccgggg cctgtgtgct atgccacaga cggggatgc atttga     777

<210> SEQ ID NO 3
<211> LENGTH: 711
<212> TYPE: DNA
<213> ORGANISM: Artificial sequence
<220> FEATURE:
<223> OTHER INFORMATION: Synthetic polynucleotide

<400> SEQUENCE: 3
```

```
cgaatgcaga ggctcctgcg atggccccgg agtgagtccc ccagaggagc cggattaggg      60
ctggaggcgg ccgagtcccc cgagaggccc ctcccgacat tcccgccccc gcgcgccgct     120
ccccgggtcc tccgcgtctc tttcccggga agcctccct cggttcctgc gcggccgcac     180
agcctggacg cagcgcacgc gggcaccggc ctgactctcc caccccgaag cctgctccca     240
acctaagtcc gccctgactc tcccagcctg aagcctgctc gccctcgggt gtccgggctg     300
ggcacaggcg ccagcgtccc cctggagagg agaggtcgcc cggcacctcc caggacaggc     360
ccaagtggga gtgggaccct cctaccttcc tgcagcctcg gcccgcgggg tgggggttg      420 ggagagatga aggaggtga ccgatcccga accatcgcct ctccattaac cagggccccgc    480 agccccgccc ctcccccaga catcgaggag ccggggaggt gtgaacggcc tcctttgtgc     540
ctctgaatcg aaggcaatta ggcgctgctt atctgggcat tagccgtgta tgcaaaccgg     600
gctcccgccc cctcctcctg ggcttataaa cgccgccgcc tggcgaggcc cgaggtggat     660
cctgcgcctg ccagccccg cctggccttc cctccggccc acctggccgc c              711
```

```
<210> SEQ ID NO 4
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 4
ttcagaatcg ccgcatgaaa cacaaacgg                                        29

<210> SEQ ID NO 5
<211> LENGTH: 61
<212> TYPE: PRT
<213> ORGANISM: Artificial sequence
<220> FEATURE:
<223> OTHER INFORMATION: Synthetic peptide

<400> SEQUENCE: 5

Ala Pro Arg Val Arg Thr Ala Phe Thr Met Glu Gln Val Arg Thr Leu
  1               5                  10                  15

Glu Gly Val Phe Gln His His Gln Tyr Leu Ser Pro Leu Glu Arg Lys
             20                  25                  30

Arg Leu Ala Arg Glu Met Gln Leu Ser Glu Val Gln Ile Lys Thr Trp
         35                  40                  45

Phe Gln Asn Arg Arg Met Lys His Lys Arg Gln Met Gln
     50                  55                  60

<210> SEQ ID NO 6
<211> LENGTH: 29
<212> TYPE: RNA
<213> ORGANISM: Artificial sequence
<220> FEATURE:
<223> OTHER INFORMATION: Synthetic oligonucleotide

<400> SEQUENCE: 6
uucagaaucg ccgcaugaaa cacaaacgg                                        29

<210> SEQ ID NO 7
<211> LENGTH: 29
<212> TYPE: RNA
<213> ORGANISM: Artificial sequence
<220> FEATURE:
<223> OTHER INFORMATION: Synthetic oligonucleotide

<400> SEQUENCE: 7
```
ucuacucaac gucuucuggc cuugccaau                                29

```
<210> SEQ ID NO 8
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 8
```
tctactcaac gtcttctggc cttgccaat                                29

```
<210> SEQ ID NO 9
<211> LENGTH: 2428
<212> TYPE: DNA
<213> ORGANISM: Homo sapiens

<400> SEQUENCE: 9
```

| | | | | |
|---|---|---|---|---|
| acctggccgc | catgcgcctc | tcctcctccc | cacctcgtgg | cccgcagcag ctctccagct | 60 |
| ttggctccgt | ggactggctc | tcccagagca | gctgctcagg | gccgacccac accccaggc | 120 |
| ctgccgactt | ctccctgggg | agcctccctg | gccaggcca | gacatccggc gcccgggagc | 180 |
| cccctcaggc | cgtcagcatc | aaggaggccg | ccgggtcctc | aaatctgcct gcgccggaga | 240 |
| ggaccatggc | cggggttgagt | aaggagccaa | ataccttgcg | gccccccgt gtccgcacag | 300 |
| ccttcaccat | ggagcaggtc | cgcaccttgg | agggcgtctt | ccagcaccac cagtacctga | 360 |
| gccctctgga | gcggaagagg | ctggccaggg | agatgcagct | ctcagaggtc cagataaaaa | 420 |
| cctggtttca | gaatcgccgc | atgaaacaca | acggcaaat | gcaggacccc cagctgcaca | 480 |
| gccccttctc | ggggtctctc | catgcgcccc | cagctttcta | ctcaacgtct ctggccttg | 540 |
| ccaatggcct | gcagctgctg | tgcccttggg | caccccctgtc | cgggcccag gctctgatgc | 600 |
| tgccccctgg | ctccttctgg | ggtctctgcc | aagtggcaca | agaggcctg gcatctgcgg | 660 |
| gagcttcctg | ctgcgggcag | cctctggcgt | cccaccccc | taccccaggc cggccttcgc | 720 |
| tgggaccagc | cctgtccacg | gggccccggg | gcctgtgtgc | tatgccacag acggggatg | 780 |
| cattttgagg | aggcacctct | gactcccaca | ctcgcgtcct | tgctgatcgc acctggctcc | 840 |
| tacctggagg | actcagttgt | tctgtttaca | tcctggtggc | acctctcacc ctgacccaca | 900 |
| caaaggttct | ggagattact | ggagaatata | tataaatata | tatatgtacg tatatatgta | 960 |
| aatacacata | tacgtatata | taaatatata | tatacatatg | tgtgtgtata tatatatata | 1020 |
| tttttttttt | tttttttttt | tttgagacgg | agtgttgctc | tgtcacccag gctggagtgc | 1080 |
| aatgacgcaa | tctcggctca | ctgcaacctc | cgcctcctgg | gttcaagcga ttctccagcc | 1140 |
| tcagcctccc | gagtagctgg | gattacagac | cccgccacc | acgcccggct aattttttct | 1200 |
| atttttagta | gaaatggggt | ttcaccatgt | tagccaggct | ggtctcaaac tcctgaccct | 1260 |
| gtgatccgcc | cgcctcggcc | tcccaaagtg | ctgggattac | aggcatgagc cactgcaccc | 1320 |
| ggccctgaga | atatatttat | taaagccacc | tcttcactga | agttaccga aagagtcggt | 1380 |
| ttaggaagga | aacgaagggt | cagtgaacag | agtcaaatgc | agaagtgggc ttgtcatggg | 1440 |
| tagggctttc | ggcgtacgat | aaaaggatca | tttgtttttt | aaaagggggtt ggaaaaactg | 1500 |
| gttttccagt | tggaaacagt | aaaggttgta | agctttgtgt | gtacaaaaga aaacagggaa | 1560 |
| tgcaggtgtg | tttatagcgt | tgtggttcaa | gtccctctta | acaagaactc caaagctgga | 1620 |
| aagcaggagg | gaacaaaggt | gaacatgaag | gcgaggatgc | tggggccctg cagtgcgctc | 1680 |

```
taggctgtgc gtgagccggg actgtaccca cagcttgctg agggctgctc ttcttgggcc    1740
agggaaagca gggcagccgg gacctgcggc tgtgcctgga ctgaagctgt cccgcaggtc    1800
cccaccctcc aacacgtgct cacctgtccc cctcctcgca gcagcctcgg gacaaaacaa    1860
tgactcaagg acagcacttc tcgcagaagg tctggaagtg cccagaatgg gaggcacgga    1920
agccctcccc ggggaggact cccgcgttga tggaccgttc ttggtgcaga ctcctgactg    1980
cgtgcatgaa acctgagaca agtgcaattc cttccatgtc gccccagagt gcccaggagg    2040
caggcagtgc ggggtgccca ggcagacggg ttcagcctgc agaactggag gcgacctgtg    2100
aaacccaccc gggcaccccca acaggaacag aagcgtggtc ctgcggctgc gtccccagcg    2160
agtttcactt tccccttgct cgtttctccc ttgttgtaag tgtttacaac tggcatgtgc    2220
ttttaaacgt caggtaagag gggaacagct gctgtacatc gtcctggcga gtgacaatgt    2280
gacagaagcc tgggcgaggc cctcggaggg cagcagctgg acaggggcta ctgggttttgg    2340 cctggacagc actgatttgt ggatgtggat gggggcacgt tgtccgtgat aaaagtacaa    2400
gtgcccctca caaaaaaaaa aaaaaaaa                                       2428
```

```
<210> SEQ ID NO 10
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 10
caaatctgcc tgcgccggag aggaccatg                                      29

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
cggactacag gggagttttg ttg                                            23

<210> SEQ ID NO 12
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 12
tccagcatcc aggtggcgac gat                                            23

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
aacccttttc cccctcgtct                                                20

<210> SEQ ID NO 14
<211> LENGTH: 20
<212> TYPE: DNA
<213> ORGANISM: Artificial sequence
```

```
<220> FEATURE:
<223> OTHER INFORMATION: Synthetic oligo nucleotide

<400> SEQUENCE: 14
agcacctgtg aggtggctgc                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
aaggcaatta ggcgctgctt                                              20

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
acagaacaac tgagtcctcc a                                            21

<210> SEQ ID NO 17
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 17
aattgaattc aatgcgcctc tcctcctcc                                    29

<210> SEQ ID NO 18
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 18
ttaatctaga tcatcaaaat gcatcccccg tctg                              34

<210> SEQ ID NO 19
<211> LENGTH: 60
<212> TYPE: PRT
<213> ORGANISM: Artificial sequence
<220> FEATURE:
<223> OTHER INFORMATION: Synthetic polypeptide

<400> SEQUENCE: 19

Arg Leu Arg Thr Ala Phe Thr Ser Asp Gln Ile Ser Thr Leu Glu Lys
1               5                   10                  15

Thr Phe Gln Lys His Arg Tyr Leu Gly Ala Ser Glu Arg Gln Lys Leu
            20                  25                  30

Ala Ala Lys Leu Gln Leu Ser Glu Val Gln Ile Lys Thr Trp Phe Gln
        35                  40                  45

Asn Arg Arg Met Lys Tyr Lys Arg Glu Ile Gln Asp
    50                  55                  60

<210> SEQ ID NO 20
```

<211> LENGTH: 258
<212> TYPE: PRT
<213> ORGANISM: Pan troglodytes

<400> SEQUENCE: 20

```
Met Arg Leu Ser Ser Ser Pro Pro Arg Gly Arg Gln Gln Leu Ser Ser
1               5                   10                  15

Phe Gly Ser Val Asp Trp Leu Ser Gln Ser Ser Cys Ser Gly Pro Thr
                20                  25                  30

His Thr Pro Arg Pro Ala Asp Phe Ser Leu Gly Ser Leu Pro Gly Pro
            35                  40                  45

Gly Gln Thr Ser Gly Ala Arg Glu Pro Pro Gln Ala Val Ser Ile Lys
        50                  55                  60

Glu Ala Ala Arg Ser Ser Asn Leu Pro Ala Pro Glu Arg Thr Val Ala
65                  70                  75                  80

Gly Leu Ser Lys Glu Pro Asn Thr Leu Arg Val Pro Arg Val Arg Thr
                85                  90                  95

Ala Phe Thr Met Glu Gln Val Arg Thr Leu Glu Gly Val Phe Gln His
                100                 105                 110

His Gln Tyr Leu Ser Pro Leu Glu Arg Lys Arg Leu Ala Arg Glu Met
            115                 120                 125

Gln Leu Ser Glu Val Gln Ile Lys Thr Trp Phe Gln Asn Arg Arg Met
        130                 135                 140

Lys His Lys Arg Gln Met Gln Asp Pro Gln Leu His Ser Pro Phe Ser
145                 150                 155                 160

Gly Ser Leu Pro Ala Pro Pro Ala Phe Tyr Ser Pro Ser Ser Gly Leu
                165                 170                 175

Ala Asn Gly Leu Gln Leu Leu Cys Pro Trp Ala Pro Leu Ser Gly Pro
                180                 185                 190

Gln Ala Leu Met Leu Pro Pro Gly Ser Phe Trp Gly Leu Cys Gln Val
            195                 200                 205

Ala Gln Glu Ala Leu Ala Ser Val Gly Ala Ser Cys Cys Gly Gln Pro
        210                 215                 220

Leu Ala Ser His Pro Pro Thr Pro Gly Arg Pro Thr Leu Gly Pro Ala
225                 230                 235                 240

Leu Ser Thr Gly Pro Arg Gly Leu Cys Ala Met Pro Gln Thr Gly Asp
                245                 250                 255

Ala Phe
```

<210> SEQ ID NO 21
<211> LENGTH: 260
<212> TYPE: PRT
<213> ORGANISM: Macaca mulatta

<400> SEQUENCE: 21

```
Met Arg Leu Ser Ser Ser Pro Pro Arg Gly Gln Gln Gln Pro Ser Ser
1               5                   10                  15

Phe Gly Ser Val Asp Trp Leu Ser Gln Ser Ser Cys Ser Gly Leu Thr
                20                  25                  30

Pro Ser Pro Arg Pro Ala Asp Val Ser Pro Gly Ser Leu Pro Gly Pro
            35                  40                  45

Gly Gln Ile Ser Gly Ala Arg Glu Pro Pro Gln Ala Ile Ser Ile Lys
        50                  55                  60

Glu Ala Val Arg Arg Ser Ala Leu Pro Ser Pro Gln Pro Ser Met Pro
65                  70                  75                  80
```

-continued

```
Gly Leu Ser Lys Glu Pro Asn Thr Leu Arg Gly Pro Arg Val Arg Thr
                85                  90                  95

Ala Phe Thr Thr Glu Gln Val Arg Thr Leu Glu Gly Val Phe Gln His
            100                 105                 110

His Gln Tyr Leu Ser Pro Leu Glu Arg Lys Arg Leu Ala Arg Glu Met
        115                 120                 125

Gln Leu Ser Glu Val Gln Ile Lys Thr Trp Phe Gln Asn Arg Arg Met
    130                 135                 140

Lys His Lys Arg Gln Met Gln Glu Val Pro Pro Asn Ser Pro Phe Leu
145                 150                 155                 160

Gly Ser Leu His Val Pro Pro Ala Phe His Ser Pro Ser Ser Gly Leu
                165                 170                 175

Ala Asn Gly Leu Gln Leu Leu Cys Pro Trp Ala Pro Leu Pro Gly Pro
            180                 185                 190

Gln Ala Leu Met Leu Pro Pro Gly Ser Phe Trp Gly Leu Cys Gln Val
        195                 200                 205

Glu Gln Glu Ala Leu Ala Ser Thr Gly Ala Ser Cys Cys Arg Gln Pro
    210                 215                 220

Leu Ala His His Pro Pro Thr Thr Gly Ser Gly Leu Pro Ala Pro Gly
225                 230                 235                 240

Pro Ala Leu Ser Thr Gly Pro Trp Gly Leu Cys Ala Leu Pro Glu Thr
                245                 250                 255

Gly Asp Ala Phe
            260
```

TREATMENT AND DIAGNOSIS OF IMMUNE DISORDERS

RELATED APPLICATIONS

This application is a continuation application of U.S. application Ser. No. 14/294,565, filed on Jun. 3, 2014, which is a divisional application of U.S. application Ser. No. 13/382,641, filed on Mar. 12, 2012, now issued as U.S. Pat. No. 8,741,865, which is the National Stage of International Application No. PCT/US2010/042126, filed on Jul. 15, 2010, which claims priority of U.S. Provisional Application No. 61/225,852, filed on Jul. 15, 2009. The contents of the prior applications are hereby incorporated by reference herein in their entirety.

BACKGROUND

The immune system defends the human body against pathogen infection, cellular transformation, and physical/chemical damage. Its dysfunction, either overactive or underactive, leads to various disorders. The dysfunction can be caused by aging, development defects, diseases, and medical treatment (e.g., chemotherapy or immuno-suppression). There is a need for drugs and reagents for treatment and diagnosis of immune disorders.

SUMMARY

This invention relates to materials and methods for treatment and diagnosis of immune disorders using Hom-1 or its inhibitors or activators. Shown below are the polypeptide and nucleotide sequences of Hom-1.

```
Hom-1 polypeptide (SEQ ID NO: 1):
mrlsssppprg pqqlssfgsv dwlsqsscsg pthtprpadf slgslpgpgq tsgareppqa vsikeaagss nlpapertma glskepntlr aprvrtaftm eqvrtleqvf qhhqylsple rkrlaremql sevqiktwfq nrrmkhkrqm qdpqlhspfs gslhappafy stssglangl qllcpwapls gpqalmlppg sfwglcqvaq ealasagasc cgqplashpp tpgrpslgpa lstgprglca mpqtgdaf (Underlined: aa. 91-151/homeodomain (SEQ ID NO: 5))

Hom-1 nucleotide sequence (SEQ ID NO: 9):
acctggccgc catgcgcctc tcctcctccc cacctcgtgg cccgcagcag ctctccagct ttggctccgt ggactggctc tcccagagca gctgctcagg gccgaccac accccaggc ctgccgactt ctccctgggg agcctccctg gcccaggcca gacatccggc gcccgggagc cccctcaggc cgtcagcatc aaggaggccg ccgggtcctc aaatctgcct gcgccggaga ggaccatggc cgggttgagt aaggagccaa ataccttgcg ggccccccgt gtccgcacag ccttcaccat ggagcaggtc cgcaccttgg agggcgtctt ccagcaccac cagtacctga gccctctgga gcggaagagg ctggccaggg agatgcagct ctcagaggtc cagataaaaa cctggtttca gaatcgccgc atgaaacaca aacggcaaat gcaggacccc cagctgcaca gccccttctc ggggtctctc catgcgcccc cagctttcta ctcaacgtct tctggccttg ccaatggcct gcagctgctg tgcccttggg caccccgtc cgggcccag gctctgatgc tgcccctgg ctccttctgg ggtctctgcc aagtggcaca agaggccctg gcatctgcgg gagcttcctg ctgcgggcag cctctggcgt cccaccccc tacccaggc cggccttcgc tgggaccagc cctgtccacg gggcccggg gcctgtgtgc tatgccacag acggggatg cattttgagg aggcacctct gactcccaca ctcgcggtct tgctgatcgc acctggctcc tacctggagg actcagttgt tctgtttaca tcctggtggc acctctcacc ctgacccaca caaaggttct ggagattact ggagaatata tataaatata tatatgtacg tatatatgta aatacacata tacgtatata taaatatata tatacatatg tgtgtgtata tatatatata tttttttttt tttttttttt tttgagacgg agtgttgctc tgtcacccag gctggagtgc aatgacgcaa tctcggctca ctgcaacctc cgcctcctgg gttcaagcga ttctccagcc tcagcctccc gagtagctgg gattacagac acccgccacc acgcccggct aattttttct atttttagta gaaatggggt ttcaccatgt tagccaggct ggtctcaaac tcctgaccct gtgatccgcc cgcctcggcc tcccaaagtg ctgggattac aggcatgagc cactgcaccc ggcctgaga atatatttat taaagccacc tcttcactga aagttaccga aagagtcggt ttaggaagga aacgaagggt cagtgaacag agtcaaatgc agaagtgggc ttgtcatggg
```

-continued

```
tagggctttc ggcgtacgat aaaaggatca tttgttttt aaagggggt ggaaaaactg gttttccagt tggaaacagt aaaggttgta agctttgtgt gtacaaaaga aaacagggaa tgcaggtgtg tttatagcgt tgtggttcaa gtccctctta acaagaactc caaagctgga aagcaggagg gaacaaaggt gaacatgaag gcgaggatgc tggggccctg cagtgcgctc taggctgtgc gtgagccggg actgtaccca cagcttgctg agggctgctc ttcttgggcc agggaaagca gggcagccgg gacctgcggc tgtgcctgga ctgaagctgt cccgcaggtc cccaccctcc aacacgtgct cacctgtccc cctcctcgca gcagcctcgg gacaaaacaa tgactcaagg acagcacttc tcgcagaagg tctggaagtg cccagaatgg gaggcacgga agccctccc ggggaggact cccgcgttga tggaccgttc ttggtgcaga ctcctgactg cgtgcatgaa acctgagaca agtgcaattc cttccatgtc gccccagagt gcccaggagg caggcagtgc ggggtgccca ggcagacggg ttcagcctgc agaactggag gcgacctgtg aaacccaccc gggcaccca acaggaacag aagcgtggtc ctgcggctgc gtccccagcg agtttcactt tccccttgct cgtttctccc ttgttgtaag tgtttacaac tggcatgtgc ttttaaacgt caggtaagag gggaacagct gctgtacatc gtcctggcga gtgacaatgt gacagaagcc tgggcgaggc cctcggaggg cagcagctgg acaggggcta ctgggtttgg cctggacagc actgatttgt ggatgtggat gggggcacgt tgtccgtgat aaaagtacaa gtgccctca caaaaaaaaa aaaaaaa (underlined: coding sequence (nt12 to
788, SEQ ID NO: 2)
```

Accordingly, in one aspect, the invention features an RNAi agent having a first strand having a first nucleotide sequence homologous to a region of a gene encoding Hom-1 protein. The RNAi agent targets an mRNA transcribed from the gene or its 5' un-translated area. In one example, the first sequence includes UUCAGAAUCGCCG-CAUGAAACACAAACGG (SEQ ID NO: 6), UCUACU-CAACGUCUUCUGGCCUUGCCAAU (SEQ ID NO: 7), and the corresponding DNA version: TTCAGAATCGCCG-CATGAAAC ACAAACGG
(SEQ ID NO: 4), TCTACT-CAACGTCTTCTGGCCTTGCCAAT (SEQ ID NO: 8), The RNAi agent can also include a second strand having a second nucleotide sequence complementary to the first sequence.

The invention also features a pharmaceutical composition having the just-mentioned RNAi agent. The composition can be a nasal aerosol or an inhalation composition.

The above-described agent and composition can be used for treating a human subject having, or at risk of having, an immune disorder, such as an inflammation disorder, including acute respiratory distress syndrome (ARDS), which can be caused by virus infection or chemicals. Specifically, one can administer to a subject in need thereof an effective amount of the RNAi agent or composition. In one embodiment, the RNAi agent has the nucleotide sequence of SEQ ID NO: 6 or 7. The subject can be one that has, or is suspected of having, an influenza, e.g., SARS.

In a second aspect, the invention features an isolated nucleic acid having SEQ ID NO: 4, 6, 7, or 8 mentioned above or its complement. The invention also features an isolated nucleic acid having the sequence listed below (SEQ ID NO: 3) or its complement.

```
5' cgaatgcagaggctcctgcgatggccccggagtgagtcccccagagg agccggattagggctggaggcggccgagtccccgagaggcccctcccga cattcccgccccgcgcgccgctccccgggtcctccgcgtctctttcccg ggaaagcctccctcggttcctgcgcggccgcacagcctggacgcagcgca cgcgggcaccggcctgactctcccaccccgaagcctgctcccaacctaag tccgccctgactctcccagcctgaagcctgctcgccctcgggtgtccggg ctgggcacaggcgccagcgtccccctggagaggagaggtcgcccggcacc tcccaggacaggcccaagtgggagtgggaccctcctaccttcctgcagcc tcggcccgcggggtgggggttgggagagatgaaaggaggtgaccgatcc cgaaccatcgcctctccattaaccagggcccgcagccccgcccctcccc agacatcgaggagccggggaggtgtgaacggcctcctttgtgcctctgaa tcgaaggcaattaggcgctgcttatctgggcattagccgtgtatgcaaac cgggctcccgcccctcctcctgggcttataaacgccgccgcctggcgag gcccgaggtggatcctgcgcctggccagccccgcctggccttccctccgg cccacctggccgcc3'
```

In a third aspect, this invention features a method for decreasing the level or activity of inflammatory cells (e.g., macrophages) in a subject. The method includes administering to a subject in need thereof an effective amount of an inhibitor of a polypeptide containing the sequence of SEQ ID NO: 1.

In a fourth aspect, this invention features a method for decreasing the level of a pro-inflammatory cytokine in a subject by administering to a subject in need thereof an effective amount of an inhibitor of a polypeptide containing the sequence of SEQ ID NO:1. Examples of the cytokine include TNF-α, IL-1β, and IL6.

In a fifth aspect, this invention features a method for treating a human subject having, or at risk of having, an immune disorder. The method includes administering to a subject in need thereof an effective amount of an inhibitor of a polypeptide containing the sequence of SEQ ID NO: 1. The immune disorder can be an inflammatory or autoimmune disorder, such as ARDS. In one example, the subject has or is suspected of having influenza.

In the above-mentioned methods, examples of the inhibitor include an antibody (such as antibody that leads to cell growth, including anti-CD3), an antisense nucleic acid, and an RNAi agent, as well as other macro molecule or small molecule compounds and naturally occurring compounds, which target Hom-1. The RNAi agent can have the nucleotide sequence of SEQ ID NO: 4, 6, 7, or 8. Examples of small molecule compounds include Prednisone, Imuran, methrotrexate, cellcept, and ionomycin, Examples of macro molecule includes PHA. In one example, each of the method further includes determining the level of Hom-1's expression or activity in a sample obtained from the subject before or after the administration so as to confirm inhibition of Hom-1.

In a sixth aspect, this invention features a method for increasing the level or activity of inflammatory cells (e.g., macrophages) in a subject. The method includes administering to a subject in need thereof an effective amount of a polypeptide containing the sequence of SEQ ID NO: 1 or 5, or a functional equivalent thereof, or a nucleic acid encoding the polypeptide, or an activator of Hom-1. Examples of the activator include 5-FU, DOX, radiation, retinoic acid, GM-CSF-IL4, resveratrol, ellagic acid, aspirin, salicylic acid, emodin and flavonoid and their derivatives that induce Hom-1 expression. In one example, the method further includes determining the level of Hom-1's expression or activity in a sample obtained from the subject before or after the administration so as to confirm induction of Hom-1.

A functional equivalent refers to a polypeptide that is similar to, or is a derivative of, a common polypeptide, e.g., a protein having one or more point mutations, insertions, deletions, truncations, a fusion protein, or a combination thereof, and retaining substantially the ability of the common polypeptide, such as binding to a LEF1/TCF. In one example, the polypeptide lacks an LEF1/TCF transcactivation domain. The cellular proliferative disorder can be a condition characterized by aberrant activation of LEF1/TCF-mediated transcription. An aberrant activation of LEF1/TCF-mediated transcription refers to a cellular condition where the LEF1/TCF-mediated transcription is abnormally high, as determined by the assays described in the example below or any analogous assays. Example of SEQ ID NO: 5's functional equivalent include the homeodomain sequences of *Xenopus* (i.e., Xom), chimpanzee, and rhesus. These homeodomain sequences are listed in FIG. 1. In general, they are at least 30% (e.g., 40, 50, 60, 65, 70, 75, 80, 85, 90, or 95%) identical to SEQ ID NO: 5. For example, the homeodomain of Hom-1 shares 68% identical and 85% positive (similar) amino acid sequence with Xom In a seventh aspect, the above-described nucleic acids can be used in a method of diagnosing an immune disorder, including (1) cellular proliferative disorder/cancer and (2) inflammatory or autoimmune disorder. Examples of the cellular proliferative disorders include acute lymphoblastic leukemia (ALL), chronic lymphocytic leukemia (CLL), and acute myloid leukemia (AML). Examples of the inflammatory or autoimmune disorder include Myelodysplastic syndromes (MDS), Systemic Lupus Erythematosus (SLE), inflammatory bowel diseases (IBD), rheumatoid arthritis (RA), and transplant rejection. The method includes the step of obtaining a biological sample from the subject; and determining the expression level of a gene encoding a polypeptide containing SEQ ID NO: 1 in the sample. The subject is determined to have or be prone to develop cellular proliferative disorder/cancer (ALL, CLL, and AML) if the expression level is below a first predetermined level or absent. The subject is determined to have or be prone to develop an inflammatory or autoimmune disorder if the expression level is above a second predetermined level. Such a predetermined level can be obtained from a normal control subject.

In an eighth aspect, the invention further features a method for managing patient treatment. The method includes steps of identifying a patient under, or in need of, a treatment for a condition, obtaining a biological sample from the patient, and determining the expression level of a gene encoding a polypeptide containing SEQ ID NO: 1 in the sample. The patient is determined to be suitable for the treatment if the level is at or above a predetermined value. Alternatively, if the level is lower than that level, the patient should not be subject to the treatment. The method can further include a step of communicating the expression level to the patient or to a physician or a caretaker of the patient. In one example, the condition is a cellular proliferative disorder, or an immune disorder, such as the above-mentioned ALL, CLL, AML, and MDS.

For ALL, CLL, AML or MDS, where the expression level of Hom-1 is lower than a predetermined value, Hom-1 can serve as a marker to direct the choice of effective treatment strategy; for transplant patients, Hom-1 can be used to ensure adequate amount of immune-suppressant is used; for auto-immune diseases, such as SLE, Hom-1 can be used to monitor the use of immune-suppressant. For example, if Hom-1 expression level decreases to a said value upon the using of immuno-suppressants, it will indicate the need to stop the usage of the immune-suppressants to avoid lymphoproliferative disorder, such as lymphoma.

In a ninth aspect, the invention features a kit for diagnosing the above-mentioned disorders or for managing patient treatment. The kit includes one or more reagents selected from the group consisting of: an antibody specific for a polypeptide having the sequence of SEQ ID NO: 1, a polypeptide having the sequence of SEQ ID NO: 1, a pair of PCR primers for amplifying a fragment of SEQ ID NO: 2 or 3, and a nucleic acid that, under a stringent condition, hybridizes to the compliment of a reference nucleic acid, wherein the reference nucleic acid consists of SEQ ID NO: 2, 3, or 5.

Stringent hybridization conditions can be suitably selected by one skilled in the art, and for example, low-stringent conditions can be given. Low-stringent conditions are, for example, 42° C., 2×SSC, and 0.1% SDS, and preferably, 50° C., 2×SSC, and 0.1% SDS. Highly stringent conditions are more preferable and include, for example, 65° C., 2×SSC, and 0.1% SDS. However, several factors other than temperature, such as salt concentration, can influence the stringency of hybridization and one skilled in the art can suitably select the factors to accomplish a similar stringency.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B are amino acid sequence alignments. FIG. 1A shows an alignment between Xom and Hom-1 homeodomain-containing regions (SEQ ID NO: 19 and residues 93-152 of SEQ ID NO:1, respectively). FIG. 1B shows an amino acid sequence alignment of Hom-1 (SEQ ID NO:1), predicted chimpanzee (SEQ ID NO: 20) and monkey Hom-1 (SEQ ID NO: 21) homologues, indicating that the Hom-1 sequence is conserved in primates.

FIGS. 3A-3D are diagrams showing results of: (A) cell viability as determined by trypan blue staining (FIG. 3A, left panel), MTS assay (FIG. 3A, middle panel), and $^3$H-thymidine incorporation assay (FIG. 3A, right panel); (B) down-regulation of Hom-1 expression with Hom-1 shRNA (FIG. 3B); (C) effects of down-regulation of Hom-1 on the proliferation of Nalm16 as measured by MTT assay (FIG. 3C, upper panel) and cell viability count (FIG. 3C, lower panel; (D) down-regulation of Hom-1, which led to elevated expression of cyclin D1, with the expression level of tubulin as an internal control (FIG. 3D).

FIGS. 4A-4D are photographs or a diagram (FIG. 4C, right panel) showing results of: (A) a tissue expression profiling of Hom-1 expression in adult tissues, using RT-PCR with GAPDH as internal control; (B) a lineage analysis showing that Hom-1 is expressed mainly in cells derived from both the myeloid and lymphoid lineages, including monocytes, T cells, B cells, and neutrophils; (C) Hom-s increasing expression during B cell development; (D) Hom-1 expression study showing that Hom-1 is not expressed in most cancer cells derived from B-cell malignancies, except Nalm16.

DETAILED DESCRIPTION

Figure 2A:
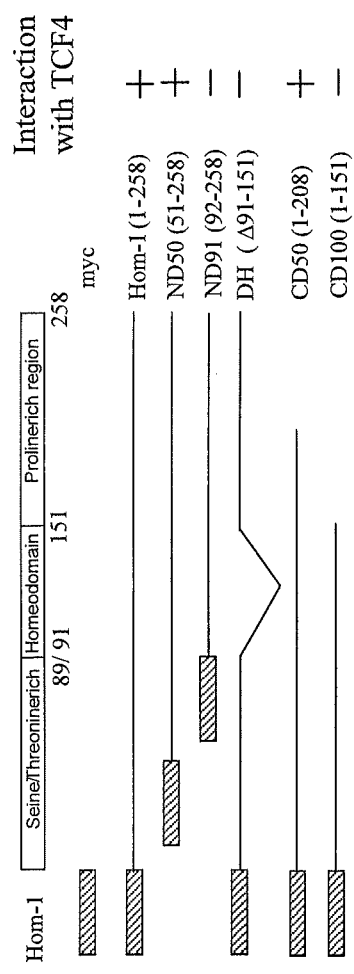
FIGS. 2A and 2B are a schematic presentation of Hom-1 and its deletion mutants and their in vivo interaction with TCF4, determined by immunoprecipitation western blot analysis (FIG. 2A) and photographs showing co-localization of Hom-1 and TCF4 in HCT116 cells (FIG. 2B).

This invention is based, at least in part, on the unexpected discoveries of that Hom-1 or its inhibitors can be used for treating or diagnosing various immune disorders.

As described herein, Hom-1 is a LEF/TCF-associated factor that represses canonical Wnt/beta-catenin signaling by disrupting the formation of the beta-catenin/LEF/TCF complex. Gain of function and loss of function approaches defined Hom-1 as a negative regulator of cell growth. Hom-1 is highly expressed in normal hematopoietic cells (and Hom-1 expression is up-regulated during maturation of hematopoietic cells), but its expression is significantly reduced in human lymphocytic leukemia and during immortalization of peripheral B lymphocytes by EBV infection. Altered expression of Hom-1 is associated with corresponding changes of the Wnt/beta-catenin/LEF/TCF target oncogenes, such as cyclin D1, suggesting Hom-1's role in the pathogenesis of various immun disorders and hematological malignancies. Accordingly, this invention features materials and methods for treating or diagnosing these disorders.

For example, a polynucleotide containing a nucleic acid sequence encoding an inhibitor of Hom-1 can be used to treat an inflammation-related disorder, such as ARDS. This inhibitor can be used as immune suppressant. The nucleic acid sequence can encode a small interference RNA (e.g., an RNAi agent) that targets Hom-1 and inhibits its expression or activity.

A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The term "RNAi agent" refers to an RNA (or analog thereof), having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and can also be used to lower or inhibit gene expression.

Thus, also within the scope of this invention is utilization of RNAi featuring degradation of RNA molecules (e.g., within a cell). Degradation is catalyzed by an enzymatic, RNA-induced silencing complex (RISC). A RNA agent having a "sequence sufficiently complementary to a target RNA sequence, e.g., Hom-1, to direct RNAi" means that the RNA agent has a sequence sufficient to trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent can also have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence. The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

The above-mentioned polynucleotides can be delivered using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

In the above-mentioned polynucleotides, e.g., expression vectors, the nucleic acid sequence encoding an inhibitor of Hom-1 is operatively linked to a promoter or enhancer-promoter combination. Suitable expression vectors include plasmids and viral vectors such as herpes viruses, retroviruses, vaccinia viruses, attenuated vaccinia viruses, canary pox viruses, adenoviruses and adeno-associated viruses.

SiRNA, miRNA, and asRNA (antisense RNA) molecules can be designed by methods well known in the art. SiRNA, miRNA, and asRNA molecules with homology sufficient to provide sequence specificity required to uniquely degrade any RNA can be designed using programs known in the art, including those maintained on websites for Ambion, Inc. and Dharmacon, Inc. Systematic testing of several designed species for optimization of the siRNA, miRNA, and asRNA sequence can be routinely performed by those skilled in the art. Considerations when designing short interfering nucleic acid molecules include biophysical, thermodynamic, and structural considerations, base preferences at specific positions in the sense strand, and homology. These considerations are well known in the art and provide guidelines for designing the above-mentioned RNA molecules for, e.g., intranasal delivery to the lungs as described in the present application.

In one aspect, the above-described agents or a composition containing the agents can be used to treat an inflammation-related disorder in a subject. An inflammatory or inflammation-related disorder is characterized by a local or systemic, acute or chronic inflammation. Examples include inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), acute respiratory distress syndrome, fulminant hepatitis, pancreatitis, hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis. Examples also include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxis or hypersensitivity responses, drug allergies, insect sting allergies, allograft rejection, and graft-versus-host disease), Sjogren's syndrome, human immunodeficiency, and virus infection.

In another aspect, Hom-1 over-expression and its activators can be used to enhance immunity so as to treat cellular proliferative disorder, such as cancer (e.g., brain, breast, prostate, colon, kidney, ovary, thyroid, lung, and hematopoietic cancer), and tumor metastasis.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model. "Treating" or "treatment" refers to administration of a compound or agent to a subject, who has a disorder (e.g., ARDS or similar respiratory tract/lung disorders), with the purpose to cure, alleviate, relieve, remedy, delay the onset of, or ameliorate the disorder, the symptom of the disorder, the disease state secondary to the disorder, or the predisposition toward the disorder. An "effective amount" refers to an amount of the compound that is capable of producing a medically desirable result, e.g., as described above, in a treated subject. The treatment method can be performed in vivo or ex vivo, alone or in conjunction with other drugs or therapy.

A composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

In one embodiment, the above-described composition can be used to treat ARDS, and similar or related respiratory tract/lung disorders. Examples include a respiratory tract or lung infection, which refers to any bacterial, viral, fungal, or parasite infection of any part of the respiratory system.

The nucleic acid molecules can be prepared in any aqueous carrier, vehicle, or solution so as to provide a composition that is pharmaceutically suitable for in vivo administration. Methods of preparing aqueous solutions are well known to one of ordinary skill in the art. Preferably, the aqueous solutions is water, physiologically acceptable aqueous solutions containing salts and/or buffers, such as phosphate buffered saline (PBS), or any other aqueous solution/surfactant acceptable for administration to a animal or human. Such solutions are well known to a person skilled in the art and include, but are not limited to, distilled water, de-ionized water, pure or ultrapure water, saline, PBS, and solutions containing usual buffers which are compatible with nucleic acids. The compositions may also contain sodium chloride and glucose or mannitol to make the solution isotonic. The composition may contain suitable auxiliary components such as pH, osmolarity and tonicity adjusting agents.

For administration via the upper respiratory tract, the composition is formulated into a solution, e.g., water or isotonic saline, buffered or unbuffered, or as a suspension, at an appropriate concentration for intranasal administration as drops or as a spray. Preferably, such solutions or suspensions are isotonic relative to nasal secretions and of about the same pH, ranging e.g., from about pH 4.0 to 7.4 or, from pH 6.0 to 7.0. Buffers should be physiologically compatible and include, simply by way of example, phosphate buffers. For example, a representative nasal decongestant is described as being buffered to a pH of about 6.2 (Remington's Pharmaceutical Sciences 16th edition, Ed. Arthur Osol, page 1445 (1980)). One skilled in the art can readily determine a suitable saline content and pH for an innocuous aqueous solution for nasal and/or upper respiratory administration. Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compositions may contain minor amounts of polymers, surfactants, or other excipients well known to those of the art. In this context, "minor amounts" means no auxiliary agents or substances are present that might affect or mediate uptake of nucleic acid in the cells of the lungs.

Aerosol dosage, formulations and delivery systems may be selected for a particular therapeutic application, as described, for example, in Gonda, Critical Reviews in Therapeutic Drug Carrier Systems, 6:273-313, 1990. The term aerosol as used herein refers to any preparation of a fine mist of particles, which can be in solution or a suspension, whether or not it is produced using a propellant. Aerosols can be produced using standard techniques, such as ultrasonication or high pressure treatment.

The formulation may be administered in an aqueous solution that is pharmaceutically acceptable for administration to the respiratory system. Particle sizes greater than 5 µm are deposited in the nasal cavity. Particles that are 2 to 10 µm can be retained in the lungs, and particles of less than 1 µm are exhaled. In preferred embodiments, the compound is administered through inhalation in a form such as liquid particles and/or solid particles. Suitable examples include, but are not limited to, an aerosol, a nebula, a mist, an atomized sample, and liquid drops. Typical apparatus which may be used for administration to humans include metered dose inhalers (MDI), nebulizers, and instillation techniques. The formulation is administered in an amount effective to treat, prevent, or diagnose on one or more symptoms or manifestations of lung disease. It is believed that the nucleic acid molecules can also be administered as dry powders using a dry powder inhaler, where the particles dissolve within the lung secretions. Various suitable devices and methods of inhalation which can be used to administer particles to a patient's respiratory tract are known in the art. Nebulizers create a fine mist from a solution or suspension, which is inhaled by the patient. See, e.g., U.S. Pat. No. 5,709,202.

The compositions are preferably delivered into the lung with a pharmacokinetic profile that results in the delivery of an effective dose of the nucleic acid. As generally used herein, an "effective amount" of a nucleic acid of the invention is that amount which is able to treat one or more symptoms of a lung disease, reverse the progression of one or more symptoms of a lung disease, halt the progression of one or more symptoms of a lung disease, prevent the occurrence of one or more symptoms of a lung disease, decrease a manifestation of the disease or diagnose one or more symptoms of a lung disease in a subject to whom the compound or therapeutic agent is administered, as compared to a matched subject not receiving the compound or therapeutic agent. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, (e.g. by means of an appropriate, conventional pharmacological protocol). In one embodiment, the compositions are delivered at a dose range of 3 to 400 µg per 20 g of body weight, with upper dosing limit of 1 gram per 20 grams body weight. In a preferred embodiment the compositions are delivered at a dose range of 50 to 100 µg per 20 g of body weight. In another preferred embodiment the compositions are delivered at a dose range of 150 nM per kg of body weight.

One or more of the above-described agents can be administered to an animal (e.g., a human) to modulate expression or activity of Hom-1 or its homologus. A physician may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the target gene mRNA (e.g. using real time PCR) or the amount of polypeptide encoded by the target gene mRNA (Western blot analysis). As is well known in the art, the dosage for a patient depends upon various factors as described above. Dosages will vary, but a preferred dosage for administration of polynucleotide is about $10^6$ to $10^{12}$ copies of the polynucleotide molecule. This dose can be repeatedly administered as needed. Routes of administration can be any of those listed above.

This invention also features diagnosis methods. A cancer cell or a cell prone to tumorigenesis can be detected in a subject based on the absence of the Hom polypeptide (e.g., antibody) or a nucleic acid (e.g., genomic DNA or mRNA) encoding the polypeptide in a test sample from the subject. In other words, the polypeptide and nucleic acids can be used as markers to indicate the presence or absence of a cancer cell. Diagnostic and prognostic assays of the invention include methods for assessing the expression level of the Hom polypeptide or nucleic acid and for identifying variations and mutations in the sequence of the Hom polypeptide or nucleic acid.

The presence, level, or absence of the Hom polypeptide or nucleic acid in a test sample can be evaluated by obtaining a test sample from a test subject and contacting the test sample with a compound or an agent capable of detecting the Hom polypeptide or nucleic acid (e.g., mRNA or genomic DNA probe). The "test sample" includes tissues, cells and biological fluids isolated from a subject, as well as tissues, cells and fluids present within a subject. The level of expression of the Hom gene can be measured in a number of ways, including measuring the mRNA encoded by the Hom gene; measuring the amount of polypeptide encoded by the Hom gene; or measuring the activity of polypeptide encoded by the Hom gene.

The level of mRNA corresponding to the Hom gene in a cell can be determined both by in situ and by in vitro formats. Messenger RNA isolated from a test sample can be used in hybridization or amplification assays that include, Southern or Northern analyses, PCR analyses, and probe arrays. One preferred diagnostic method for the detection of mRNA levels involves contacting the isolated mRNA with a nucleic acid probe that can hybridize to the mRNA encoded by the Hom gene. The probe can be a full-length Hom nucleic acid, such as the nucleic acid of SEQ ID NO: 2 or 3 or a portion thereof, such as an oligonucleotide of at least 10 nucleotides in length and sufficient to specifically hybridize under stringent conditions to Hom mRNA or genomic DNA.

In one format, mRNA (or cDNA prepared from it) is immobilized on a surface and contacted with the probes, for example, by running the isolated mRNA on an agarose gel and transferring the mRNA from the gel to a membrane, such as nitrocellulose. In another format, the probes are immobilized on a surface and the mRNA (or cDNA) is contacted with the probes, for example, in a gene chip array. A skilled artisan can adapt known mRNA detection methods for detecting the level of Hom mRNA.

The level of mRNA (or cDNA prepared from it) in a sample encoded by Hom gene can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to genomic DNA on chromosomes or mRNA that encodes the Hom polypeptide.

In another embodiment, the methods of the invention further include contacting a control sample with a compound or agent capable of detecting Hom mRNA, or genomic DNA, and comparing the presence of Hom mRNA or genomic DNA in the control sample with the presence of Hom mRNA or genomic DNA in the test sample.

The above-described nucleic acid-based diagnostic methods can provide qualitative and quantitative information to determine whether a subject has or is predisposed to a disease associated with aberrant Hom gene expression, e.g., cancers.

A variety of methods can be used to determine the level of Hom polypeptide. In general, these methods include contacting an agent that selectively binds to the polypeptide, such as an antibody, to evaluate the level of polypeptide in a sample. Antibodies can be polyclonal, or more preferably, monoclonal. An intact antibody, or a fragment thereof (e.g., Fab or F(ab')$_2$) can also be used. In a preferred embodiment, the antibody bears a detectable label. The term "labeled", with regard to the probe or antibody, is intended to encompass direct labeling of the probe or antibody by physically linking a detectable substance to the probe or antibody, as well as indirect labeling of the probe or antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include radio isotopes (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles by the Quantum Dot Corporation, Palo Alto, Calif.).

The detection methods can be used to detect the Hom polypeptide in a biological sample in vitro as well as in vivo. In vitro techniques for detection of the Hom polypeptide include ELISAs, immunoprecipitations, immunofluorescence, EIA, RIA, and Western blotting analysis. In vivo techniques for detection of the Hom polypeptide include introducing into a subject a labeled anti-Hom antibody. For example, the antibody can be labeled with a detectable substance as described above. The presence and location of the detectable substance in a subject can be detected by standard imaging techniques.

The diagnostic methods described herein can identify subjects having, or at risk of developing, a disease or disorder associated with aberrant Hom expression or activity. As described herein, examples of such a disease or disorder include ALL, CLL, AML, and MDS The prognostic assays described herein can be used to determine whether a subject is suitable to be administered with an agent (e.g., an agonist, antagonist, peptidomimetic, protein, peptide, nucleic acid, small molecule, or other drug candidate) to treat a disorder, such as cancer (e.g., ALL, CLL, and AML). For example, such assays can be used to determine whether a subject can be administered with a cytotoxic drug to treat a cell proliferation disorder or immune-suppressants to treat an immune disorder, including those involved in organ/tissue transplantation.

Thus, also featured in this invention is a method of monitoring a treatment for a cancer or an immune disorder in a subject. For this purpose, gene expression levels of Hom can be determined for test samples from a subject before, during, or after undergoing a treatment. An increase of the expression level of Hom after the treatment indicates that the subject can be further treated by the same treatment. For example, a patient who has received organ or tissue transplantation often faces the problems of organ or tissue rejection. That is, the body has an immune response to an organ or tissue which causes failure of the transplant. To address this problem, organ or tissue transplantation is often accompanied by nonspecific immune suppression therapy to prevent T cell-mediated rejection. However, these immunosuppressants can cause infection, hypertension, cancer, and other undesirable side effects. Therefore, there is a need for monitoring the suppression. To that end, Hom-1 expression level can serve as a marker for a proper level or degree of immune suppression. A skilled in the art can adjust the amount of immunosuppressants and length of treatment based on the level of Hom-1 expression during the course of the treatment.

Information obtained from practice of the above assays is useful in prognostication, identifying progression of, and clinical management of diseases and other deleterious conditions affecting an individual's health status. In preferred embodiments, the foregoing diagnostic assays provide information useful in prognostication, identifying progression of and management of malignancies (cancers) that are characterized by lack or abnormal low level Hom expression. The information more specifically assists the clinician in designing chemotherapeutic or other treatment regimes to eradicate such malignancies from the body of an afflicted mammal, e.g., a human.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example 1 Hom-1, a LEF/TCF-Associated Transcription Repressor, is a Tumor Suppressor LEF/TCFs transcriptional factors are the nuclear transcriptional mediators of canonical Wnt/beta-catenin signaling, which is critical to cell fate determination in early embryogenesis and is implicated as a major oncogenic pathway in a variety of cancers. LEF/TCFs possess little intrinsic transcriptional activity, but are tightly controlled by associated factors. In the presence of Wnt signaling, LEF/TCFs form a complex with beta-catenin, which drives the expression of LEF/TCF downstream genes, including well-established oncogenes such as cyclin D1 and C-myc. Xom (also known as Vent-2, Xbr-1, and Vox) is a vertebrate homologue of the *Drosophila ananassae* homeobox gene Om1D. Xom was identified as the major downstream mediator of BMP4 and is an essential constituent of the ventral signaling center. Similar to beta-catenin, Xom also is an unstable protein. We examined the effect of Xom on LEF/TCF-mediated transcription and identified Xom as a novel LEF/TCF-associated transcription factor.

In this example, through sequence homology searching, distribution proliling, and functional analysis, we identified a new transcript called Hom-1 as a candidate human Xom homolog. It was found that Hom-1 shares the same ORF with the previously known VentX2 but contains a 711-bp 5'UTR beyond the known sequence of VentX2. Further assays were conducted to analyze Hom-1 as described below.

Materials and Methods:
Promoter-Luciferase Assay

For a typical promoter-luciferase assay experiment, $2\times10^5$ 293 T cells were seeded onto a 12-well culture plate 24 hours prior to transfection. One microgram of a plasmid encoding gene of interest and 0.3 µg luciferase-reporter construct were mixed with 3 µl of liposome transfection reagent (TRANSIT, Mirus) and transfected into cultured cells following the manufacture's instructions. Forty-eight hours post transfection, cells were washed with PBS and lysed with a 1× cell lysis buffer (PROMEGA), scraped, and collected on ice. After a brief spin in a table-top centrifuge, 20 µl of supernatants were mixed with 100 µl of luciferase assay reagent (PROMEGA), and luciferase activity was measured using a TR717 Microplate luminometer (APPLIED BIOSYSTEM).
RNA Isolation, RT-PCR and Real-Time PCR Total RNA was extracted by the TRIzol method. Cells ($1\times10^6$) were homo-genized in 1 ml Trisol, and 200 ml chloroform was then added. After vortex mixing, the samples were centrifuged at 12,000 rpm, and the supernatants were collected in new tubes. Isoproponol (500 ml) was added to each sample, mixed, and kept at room temperature for 30 minutes. Samples were then centrifuged at 12,000 rpm at 4° C. for 30 minutes. The pellets were collected, washed with 70% ETOH, air-dried, and re-suspended in 20 µl of DEPC-treated H2O. The final RNA concentration was determined by OD260 measurement. First-strand cDNA was synthesized with the SuperSript First-Strand Synthesis System (INVITROGEN) according to the manufacturer's protocol. Briefly, 3 µg of total RNA from each sample was used for RT-reaction, and 1 µl of the RT product was used for PCR reaction. GAPDH was used as an internal control. The identities of PCR products were verified by sequencing. Real-time PCR was performed using the LightCycler System (ROCHE) and the LightCycler FastStart DNA Master SYBR Green I, according to manufacturer's instructions. The relative levels of gene expression were calculated by the formula: relative gene expression=2−ΔCd (ΔCd=cycle of the specific gene—cycle of the reference GAPDH gene).
Splicing Cloning of Hom-1 and 5' cDNA Walking The Hom-1 genomic DNA of 2.4 kb was amplified from a BAC RP13 clone containing the Hom-1 genomic sequence with PCR reaction using primers

F1:
(SEQ ID NO: 17)
5' AATTGAATTCAATGCGCCTCTCCTCCTCC 3',

R1:
(SEQ ID NO: 18)
5' TTAATCTAGATCATCAAAATGCATCCCCCGTCTG 3'.

The PCR products were digested with EcoRI and XbaI and cloned into the CS2 vector. The plasmid was transfected into 293T cells. Total RNA from the transfected cells was extracted by TriZol methods and subjected to RT reaction using the SuperScript First-Strand Synthesis System (INVITROGEN). The RT products were amplified with primer F1 and R1, digested with EcoRI and XbaI, and then cloned into the CS2 vector.

For 5' cDNA walking, first-strand cDNA was amplified using total RNA from peripheral leucocytes from healthy volunteers. The 5' un-translated region was amplified with forward primers starting at position-100, -161, -291, -357, -471, -711, -843 (the position of the nucleotide "A" of the start codon ATG was designated as position 0).
Immunofluorescence and Co-Immunoprecipitation For immunofluorescence experiments, GFP-Hom-1 and Myc-TCF4 were co-transfected into HCT116 cells with TransIT (MIRUS). TCF4 was stained with anti-myc antibody, followed by secondary Alexa 568 labeled goat anti-mouse antibody (INVITROGEN). Nuclei were visualized with DAPI and images were taken with co-focal microscopy at the core facility of Children's Hospital Boston. For co-immunoprecipitation, affinity protein A/G beads were prepared by mixing 20 µl of protein A/G agarose beads (SANTA CRUZ BIOTECHNOLOGY) with 1 µg of the antibodies of interest. To prepare the cell lysates, $2\times10^6$ of cells were lysed with a 1× cell lysis buffer (PROMEGA) containing 1× protease inhibitor reagent (ROCHE). The cell lysates were incubated on ice for 30 minutes, briefly sonicated, and centrifuged at 12,000×g for 5 minutes at 4° C. The supernatants were further cleaned by adding 20 µl of protein A/G agarose beads and 1 µg of pre-immune serum at 4° C. for two hours. After a brief spin, the supernatants were then mixed with 20 µl of antibody-labeled-protein A/G beads at 4° C. overnight. The beads were washed four times with PBS 0.2% NP40. Bound proteins were released by 2× sample buffer, boiled at 95° C. for 5 minutes, centrifuged briefly, and subjected to western blot analysis using specific antibodies as indicated. Mouse anti-myc antibody and goat anti-TCF4 were purchased from Santa Cruz.

Cell Culture, Cell Isolation, and cDNA Array

Cells used in this example include Nalm6 cells, Nalm16 cells, Reh cells, RS11 cells, H Sultan cells, ALL sample cells, CLL sample cells, 293T cells, Jurkat cells, Tall cells, EBV transformed B cells and matched B cells from healthy individuals, PC3 cells, LnCap cells, MCF7 cells, MDA cells, SK-N-AS cells, H1299 cells, H460 cells and 116 cells. All the cell lines were maintained in RPMI 1640 or DMEM supplemented with 10% FBS and 1% penicillin and streptomycin. Leucocytes from healthy individuals were isolated from discarded leukopaks from healthy anonymous blood donors at Children's Hospital Boston. Experiments with human materials were performed in accordance with guidelines approved by the institutional review committee of Brigham and Women's Hospital.

T cells, B cells, granulocytes, and monocytes were isolated with MCAS microbeads specifically labeled with CD3, CD19, CD15, and CD14 antibodies (MILTENYI BIOTEC), following the manufacturer's instructions. PrimeExpress II Human Normal Tissue cDNA Panel (#10020) was purchased from PRIMGEN.

Transient Transfection and Establishment of Hom-1 shRNA Stable Cell Lines

For HCT116 and 293T cells, all transient transfections were performed with liposomal TransIT reagent (Mirus) following manufacturer's instructions. For Reh and Nalm16 cells, transient transfection was performed with electroporation using the Cell Line Nucleofector Kit V (cells) following manufacturer's instructions. Hom-1 shRNA plasmids were obtained from Origene Technologies; Construct 1: 5' CAAATCTGCCT GCGCCG GAGAGGACCATG 3' (SEQ ID NO:10); construct 3: 5' TTCAGAATCGCCGCAT-GAA ACACAAACGG 3' (SEQ ID NO: 4). To establish Hom-1 knock-down cell lines, cells were transfected with Hom-1 shRNA. Forty-eight hours post-transfection, the Hom-1 knock-down cells were selected with 500 ng/ml puromycin treatment for four weeks.

Cell Viability Assays, MTS Proliferation Assays, and $^3$H Thymidine Incorporation Assays For Hom-1 over-expression experiments, cells were transfected with plasmids encoding GFP-Hom1 or GFP. Twenty-four hours post-transfection, GFP-positive cells were sorted out by FAC G4 Sort Flow Cytometer (BD BIOSCIENCE) and seeded into culture plates.

For cell viability assays, $5 \times 10^5$ cells were seeded into 12-well plates in triplicate. Viable cells were counted four times by Trypan Blue staining at each indicated time point. Cell viability is presented as a percentage. For MTS proliferation assays, $1 \times 10^5$ cells were seeded into 96-well plates in triplicate. Forty-eight hours post-seeding, cell proliferation rate was measured with the Cell Titer 96 Aqueous No-radioactive cell proliferation assay kit (PROMEGA) according to manufacture's instructions. For $^3$H thymidine incorporation assays, $1 \times 10^5$ sorted cells were seeded into 96-well culture plates in triplicate. Forty-eight hours post-seeding, $^3$H thymidine (1.0 U$^{ci}$/well) was added into each well for an additional 18 hours. The cells were lysed by freezing at −70° C. overnight, transferred to membrane, washed with PBS three times, and subjected to scintillation counting using the TopCount NXT (PACKARD BIOSCIENCE).

CHIP Assay

Hela cells were cultured in 6 cm dishes for 24 hours and then transfected with constructs encoding myc-Hom-1 or myc-tag. Twenty-four hours post-transfection, the chromatin immunoprecipitation (ChIP) assay was performed using an assay kit (Upstate Cell Signaling) following manufacture's instructions. Cyclin D1 promoter sequence was amplified with specific primers: F5'-CGGACTACAGGG-GAGTTTTGTTG-3' (SEQ ID NO:11) and R5'-TCCAG-CATCCAGGTGGCGACGAT-3' (SEQ ID NO:12), and immunoglobulin heavy chain promoter was amplified with specific primers: F5'-AACCCTTTTCCCCCTCGTCT-3' (SEQ ID NO:13), R5'-AGCACCTGTGAGGTGGCTGC-3' (SEQ ID NO:14). PCR products were analyzed by electrophoresis on 1% agarose gels.

Statistical Analysis

Data were analyzed using the t test. The differences with p value <0.05 were considered statistically significant Results:

Hom-1 is a Xom homologue

To identify the human homologue of Xom, we used the amino acid sequence of the Xom homeodomain (HD) as the template to search against the NCBI protein database. The candidate gene revealed by the search was designated Hom-1 (previously known as Ventx2). The open reading frame of Hom-1 encodes 258 amino acids, in comparison with the 327 amino acids of Xom. As shown in FIG. 1A, the homeodomain of Hom-1 shares 68% identical and 85% positive (similar) amino acid sequence with Xom. Hom-1 contains an N-terminal serine/threonine-rich domain (aa 4-89), a homeodomain (aa. 91-151), and a C-terminal proline-rich domain (aa. 151-258). This is similar to Xom, which also contains an N-terminal serine/threonine-rich domain (aa. 31-154), a homeodomain (aa. 172-233), and a C-terminal proline-rich domain (aa. 233-326).

Using the Vector NTI protein alignment program, we found that, besides the homeodomain, Hom-1 and Xom share strong similarities at the carboxyl terminal region and the beginning portion of the amino terminal region for about ten amino acids. There is an unaligned portion of the N-terminal region between these two molecules that is also functionally relevant. Comparative genomic analysis shows that Hom-1 is preserved in primates (FIG. 1B), but sequence homology is lost in other species. Besides structural similarities, EST data from CGAP (The Cancer Genome Anatomy Project) show that the expression pattern of Hom-1 is similar to the distribution of Xom, both demonstrating very limited expression in adult tissues but expression in embryonic tissues.

To further evaluate the function of Hom-1, its cDNA was obtained through splicing cloning, using the BAC RP13 clone as the template. In addition to the known sequence, a novel 5' untranslated region of 711 bp on the first exon of Hom-1 was identified by 5'-cDNA walking.

Xom is a transcriptional repressor of the dorsal-specific gene Goosecoid. To identify any potential functional similarity between Hom-1 and Xom, mRNA encoding Hom-1 or Xom was injected into one of the two blastomeres of *Xenopus* embryos at the two-cell stage, together with mRNA encoding Activin and the Gsc-luciferase reporter construct. Five embryos were collected at stage 10, and luciferase activity was measured using the PROMEGA luciferase assay system.

It was found that expression of Hom-1 inhibited activin-induced expression of the Gsc-promoter, similar to the inhibition of Gsc-promoter by Xom. These results are consistent with the prior finding that expression of Hom-1/Ventx2 inhibits dorsalization in Zebrafish. Nevertheless, as shown below, Xom transactivates LEF/TCF-mediated transcription through its N-terminal domain, which distinguishes Xom from Hom-1. Thus, it is concluded that Hom-1 is a Xom homologue rather than a Xom ortholog.

Hom-1 forms a complex with Lef/Tcf transcriptional factors

Figure 2B:
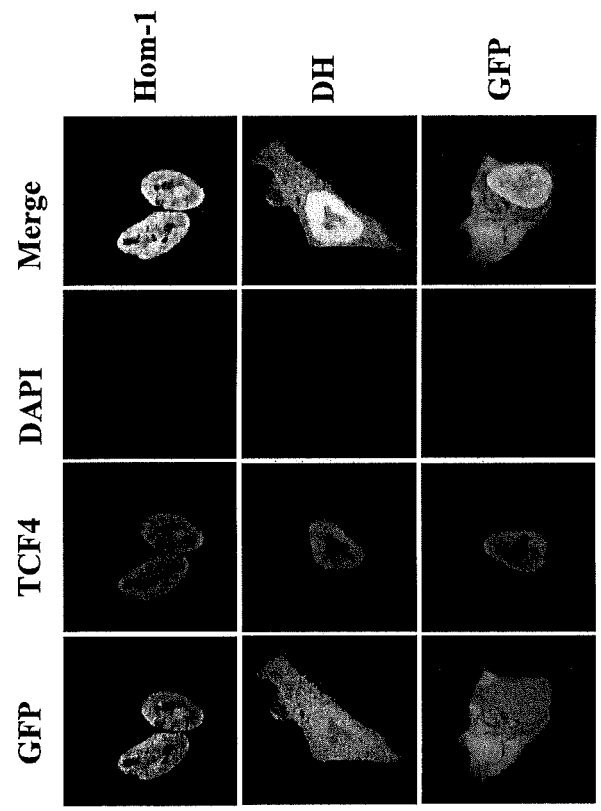

It was examined whether Hom-1 interacts with LEF1/TCFs. Myc-tagged Hom-1 was transiently expressed in HCT116 cells, and potential interaction between Hom-1 and TCF4 was characterized by co-immuno-precipitation. When anti-TCF4-coated beads were applied to the HCT116 cell extracts, myc-Hom-1 readily co-immuno-precipitated with TCF4. It was also found that Hom-1 co-localized with TCF-4 in a punctate manner in the nuclei of transfected cells (FIG. 2B). To determine the critical domains of Hom-1 involved in the interaction with Lef/Tcf factors, a serial deletion mutants of Hom-1 was made and tested their affinity with TCF4 (FIG. 2A). It was found that if the homeodomain and its surrounding region of 50 amino acids were deleted from Hom-1, the resultant mutants did not interact with anti-TCF4-coated beads by co-immunoprecipitation, suggesting that the Hom-1 homeodomain and its surrounding region play critical roles in the interaction between Hom-1 and LEF1/TCF factors.

Given that the homeobox domain is a DNA binding domain of Hom-1, 20 µg/ml ethidium bromide (EtB) was included to rule out a possible interference of nuclear acids in the interaction between Hom-1 and TCF4. It was found that EtB did not interrupt the interaction between TCF4 and Hom-1, indicating that the interaction between Hom-1 and TCF4 is not dependent on their association with DNA.

Hom-1 Inhibits Beta-Catenin Transactivation of Lef/Tcf-Mediated Transcription

Assays were conducted to examine the effects of Hom-1 on beta-catenin transactivation of LEF/TCFs, using the LEF/TCF reporter TOPflash assay. It was found that Hom-1 alone did not activate LEF1/TCF-mediated transcription in 293T cells. Instead, Hom-1 blocked β-catenin transactivation of LEF/TCF-mediated transcription in a concentration-dependent manner To further confirm the inhibitory effects of Hom-1 on beta-catenin signaling, assays were conducted to examine the effects of Hom-1 on LEF/TCF-mediated transcription in HCT116 cells, which constitutively express elevated endogenous β-catenin activity. The results show that Hom-1 inhibited LEF1/TCF-mediated transcription in a concentration-dependent manner in HCT116 cells, but exerted no significant effects on the expression of beta-catenin mRNA or protein.

To explore the alternative mechanisms underlying Hom-1 action, it was examined whether Hom-1 disrupts the formation of a beta-catenin and TCF4 complex, which is required for beta-catenin transactivation of LEF/TCF target genes. HCT116 cells were transiently transfected with Myc-Hom-1 in increasing concentrations. Forty-eight hours post-transfection, HCT116 cell lysates were collected, and TCF4 was immunoprecipated with specific antibody. Specific antibodies were used to detect any Hom-1 and beta-catenin in the immunocomplex. It was found that, with increasing levels of Myc-Hom-1 in the immunocomplex, the levels of beta-catenin in the immunocomplex exhibited a corresponding decrease, suggesting that Hom-1 expression disrupts formation of the beta-catenin/TCF4 complex.

Thus, similar to the actions of beta-catenin-associated inhibitors of beta-catenin/LEF/TCF signaling such as the Chibby, blocking formation of a complex between beta-catenin and LEF/TCF factors could explain Hom-1 inhibition of LEF/TCF transactivation by beta-catenin.

Hom-1 Modulates the Expression of Beta-Catenin/LEF1/TCF Downstream Genes

In this part, assays were conducted to examine the effects of Hom-1 on the expression of endogenous LEF/TCF target genes, such as cyclin First, assays were conducted to examine the interaction between Hom-1 and the cyclin D1 promoter, using a CHIP assay. A plasmid encoding myc-Hom-1 and the control myc-tag were transiently transfected into Hela cells, which were later subjected to immunoprecipitation with antibodies against myc-tag. The cyclin D1 promoter or IgG heavy chain promoter Cmµ, □□ which was used as a negative control, were amplified with specific primers. It was found that Hom-1 bound specifically to the Cyclin D1 promoter, but not the control Cmµ promoter.

Further, the effects of Hom-1 on the expression of Cyclin D1 were tested, using the cyclin D1 promoter-luciferase assay. Consistent with Hom-1 inhibition of LEF/TCF-mediated transcription, it was found that Hom-1 blocked transactivation of the Cyclin D1 promoter-luciferase construct in HCT116 cells, similar to its effect on the TOPflash reporter construct. Consistent with an inhibitory effect of Hom-1 on the expression of cyclin D1, western blot analysis showed that Hom-1 caused a concentration-dependent decrease in levels of the intra-cellular cyclin Hom-1 is a Negative Regulator of Cell Proliferation The canonical Wnt/beta-catenin/LEF/TCF pathway has been implicated in malignant transformation and cell proliferation. In this part, assays were carried out to assess Hom-1's role in cell proliferation.

The expression of Hom-1 was screened in cancer cells derived from both solitary and hematopoietic malignancies by RT-PCR. Hom-1 expression was identified only in the Nalm16 lymphoblastic leukemia cells but not other cancer cells (see below and FIG. 4D).

To determine the effect of Hom-1 on cell proliferation, GFP-Hom-1 was transiently transfected into Reh lymphoblastic leukemia cells, which does not express endogenous Hom-1. The positively transfected cells were sorted with FACS, and the effects of Hom-1 on cell proliferation were determined by cell count, MTT metabolic assay, and DNA synthesis $^3$H thymidine incorporation assay (FIG. 3A). The results indicated that Hom-1 expression strongly inhibited the proliferation of Reh cells. Similar results were also obtained with Hom-1 on the proliferation of other cancer cells.

To further evaluate the effect of Hom-1 on cell proliferation, the expression of Hom-1 was down-regulated in Nalm16 cells using a shRNA technique. Four constructs of Hom-1 shRNA were transfected into the Nalm16 cells. The effectiveness of these constructs in down-regulating Hom-1 expression were determined by RT-PCR and were further verified with western blot analysis, using a specific Hom-1 antibody raised in the laboratory. It was found that, while construct 3 had high specific activity against Hom-1 expression, construct 1 exerted little effect (FIG. 3B) Subsequently, the constructs were used to transfect Nalm16 cells, and positively transfected cells were selected by puromycin resistance. The effect of these Hom-1 shRNA on the expression of endogenous Hom-1 was determined by RT-PCR (FIG. 3B upper panel). Expression of Hom-1 in control and Hom-1 shRNA transfected cells was further determined by immunoblot using Hom-1-specific antibody (FIG. 3B middle panel) and quantified by densitometry (FIG. 3B lower panel). The results indicated that construct-3 but not construct-1 effectively knocks down the expression of Hom-1 in Nalm16 cells.

The effects of Hom-1 on cell proliferation were further determined by cell proliferation assay and MTT assay. As shown in FIG. 3C, while downregulation of Hom-1 with construct 3 was associated with hyper-proliferation of Nalm16, neither the control construct nor construct 1 had any effect on the proliferation of Nalm16 cells. The above results suggested that Hom-1 is a negative regulator of cell proliferation.

To determine whether the effects of Hom-1 on cell proliferation relate to the expression of LEF/TCF target genes, the effects of down-regulating Hom-1 on the expression of cyclin D1 was examined. In contrast to the effect of overexpression, down-regulation of Hom-1 was associated with increased cellular levels of cyclin D1 (FIG. 3D). The above results suggested that Hom-1 down-regulated cell proliferation at least partly through inhibiting beta-catenin/LEF/TCF signaling and the expression of its downstream cell cycle regulators such as cyclin Hom-1 Expression is Highly Regulated in Hematopoietic Cells and Implicated in Oncogenesis of Lymphocytic Leukemia To explore the physiological role of Hom-1, its expression was characterized in adult tissues, using tissue cDNA array and RT-PCR. It was found that the expression of full length Hom-1 was highly restricted to peripheral blood leukocytes (FIG. 4A). Lineage analysis of peripheral blood leukocytes showed that Hom-1 was expressed in both myeloid and lymphoid lineages, including mononuclear cells, B cells, T cells, and neutrophils (FIG. 4B). Its expression increased as B cells matured (FIG. 4C). In contrast to the physiological expression of Hom-1 in peripheral B lymphocytes, Hom-1 was essentially not expressed in cancer cell lines derived from B cell malignancies, except for Nalm16 cells (FIG. 4D). Moreover a screen of cancer cell lines derived from solitary cancers revealed that Hom-1 was not expressed in cancer cell lines, including HCT116, SW480, HT29, HepG2, PC3, LnCap, Hela, H460, H1299, MCF7, MDA and SK-N-AS. LEF/TCF factors have been shown to play an essential role in B-lymphocyte development and leukemogenesis. Consistent with Hom-1's role in oncogenesis of B cell malignancies, the level of full length Hom-1 expression was significantly reduced during the immortalization of peripheral B cells by EBV infection.

Figure 5A:
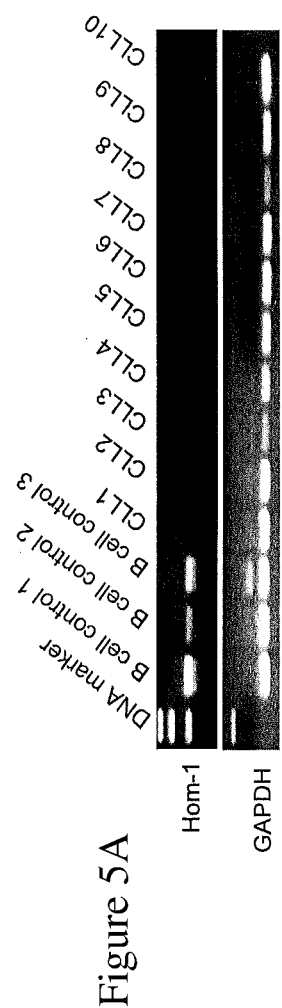
FIGS. 5A and 5B are (A) a photograph showing that Hom-1 expression was markedly reduced in peripheral blood samples from newly diagnosed ten CLL patients (FIG. 5A) and (B) a diagram showing that down-regulation of Hom-1 in lymphocytic leukemia was associated with corresponding elevation in the expression of cyclin D1 with GAPDH used as internal control (FIG. 5A).
Figure 5B:
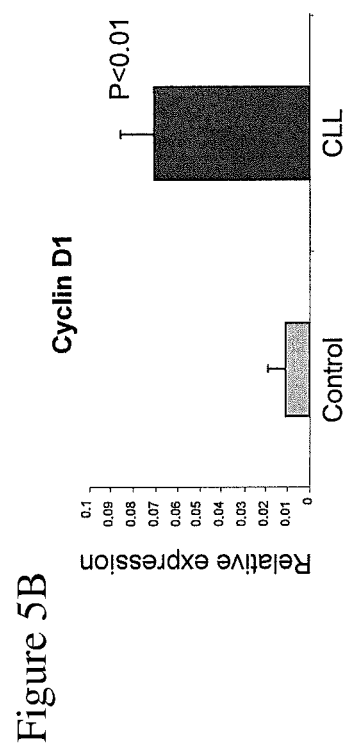

To further explore the role of Hom-1 in the oncogenesis of B cell malignancies, the expression of full length Hom-1 was examined in peripheral blood samples from patients with newly diagnosed and untreated acute lymphoblastic leukemia (ALL) and chronic lymphocytic leukemia (CLL). All CLL samples contained a minimum of 95% CD19+ leukemia cells. RT-PCR of the total RNA level from these blood samples showed a significant reduction of Hom-1 expression in all seven ALL and ten CLL samples (FIG. 5A). It was also found that down-regulation of Hom-1 expression in the peripheral blood of acute and chronic leukemia patients was associated with an elevation in the expression of cyclin D1 (FIG. 5B).

Several mechanisms could explain the highly regulated expression of Hom-1. Besides transcriptional regulation, the Hom-1 transcript contains a long GC-rich 5' un-translated region (5'UTR) of 711 base pairs. A long atypical 5'UTR is seen in about 10% of mRNAs and often precedes genes that regulate cell growth and proliferation, such as C-myc, HIF, and LEF/TCF. The long 5'UTR could form a secondary structure to regulate translation initiation of Hom-1. Thus, it is possible that Hom-1 5'UTR plays a critical role in regulating the expression of Hom-1 at the translational level.

The above results suggested that Hom-1 is a tumor suppressor functioning, as least partly, as an inhibitor of the expression of LEF/TCF-downstream oncogenes such as cyclin DE The results also suggested that Hom-1 can be used for predicting clinical behavior of lymphocytic leukemia and as a target for identifying drugs for treating various disorders, e.g., cancer.

Example 2: Hom-1 Induced Apoptosis in p53-Sufficient and -Deficient Cancer Cells Materials and Methods
Cell Culture, Transfection, Chemotherapy The human colorectal cancer lines HCT116, SW480, and the human lung cancer cell line H460 and H1299 were obtained from America Type Culture Collection (Manassas, Va.). The HCT116 ($p53^{-/-}$) cell line was a gift. All cell lines were maintained at 37° C. and 5% $CO_2$. Cell culture media included McCoy's 5A (INVITROGEN, Carlsbad, Calif.) for HCT116, HCT116 ($p53^{-/-}$) and SW480, RPMI-1640 (INVITROGEN) for H460 and H1299. The cell culture media were supplemented with 10% fetal bovine serum (HYCLONE, Logan, Utah), 100 units/ml penicillin, 100 μg/ml streptomycin, and 250 ng/ml amphotericin B (MEDIATECH, Herndon, Va.). Transfection was done with Lipofectamine 2000 (INVITROGEN) following the instructions of the manufacturer. The anticancer drugs used in the study, including 5-fluorouracil (5-FU, 50 ug/ml) and doxorubicin hydrochloride (DOX, 0.4 ug/ml) were purchased from SIGMA (ST. Louis, Mo.). All drugs were dissolved in DMSO and diluted to appropriate concentrations with cell culture media.

Plasmids and Construction

A nucleic acid encoding Hom was subcloned by PCR-based technique into the pCS2+ vector, GFP-tag. The constructs were verified by in vitro translation and sequencing.

Confocal Microscopy

HCT116 cells were seeded on glass chamber slides and transfected with Hom-GFP expression constructs. Twenty-four hours later, the cells were fixed with paraformaldehyde in PBS, and counterstained by propidium iodide (PI, SIGMA). After four washes in PBS for 5 min each, the slides were mounted and analyzed by confocal microscopy.

Apoptosis and Growth Assay

Cells including attached plus floating cells in the medium were harvested and fixed in a solution containing a final concentration of 3.7% formaldehyde, 0.5% Nonidet P-40, and 10 μg/ml 4',6-diamidino-2-phenylindole in PBS. Apoptosis was assessed through microscopic visualization of condensed chromatin and micronucleation. At least three independent experiments were carried out for each condition, and a minimum of 400 cells were counted in each measurement.

Cell growth was measured by 3-(4,5-dimethyl-thiazol-2yl)-5-(3-carboxymethoxyphenyl)-2-(4-sulfophenyl)-2H-tetrazolium (MTT) assay in 96-well plates (8,000 cells per well) using the CellTiter 96 AQueous One Solution (PROMEGA, Madison, Wis.) following the instructions of the manufacturer. $A_{490\ nm}$ was measured using a VERSAmax Tunable Microplate Reader (Sunnyvale, Calif.). Vehicle-treated cells were as 1 (100%). Each experiment was done in triplicate and repeated at least twice.

Colony Formation Assay

Cells were transfected with Lipofectamine 2000 (INVITROGEN) for 24 h in 100 mm cell culture dishes according to the instructions of the manufacturer. Then, the cells were collected, and sorted GFP-Vector or GFP-Hom1 positive cells using a FAC G4 sort flow cytometer (BD Biosciences). These GFP-positive cells were plated in six-well plates at dilutions of $1 \times 10^5$ cells each well. Cells were allowed to grow for 5-10 days before staining with Crystal Violet (SIGMA). All experiments were repeated at least twice, and similar results were obtained in each trial.

Xenograft Tumors and Tissue Staining

All animal experiments were approved by the Institutional Animal Care and Use Committee at the Harvard Medical School. Cells were transfected with Lipofectamine 2000 (INVITROGEN) for 24 h in 100 mm cell culture dishes. Then, the cells were collected, and sorted vector-GFP or Hom-GFP positive cells using a FAC G4 sort flow cytometer (BD BIOSCIENCES). Xenograft tumors were established by s.c. injection of $1 \times 10^5$ vector-GFP or Hom-GFP positive HCT116 ($p53^{+/+}$) or HCT116 ($p53^{-/-}$) cells into both flanks of 5- to 6-week-old female athymic nude mice (SIMONSEN LABORATORIES, Gilroy, Calif.). At the same time, unsort cell $1 \times 10^6$ including GFP-positive and -negative cells also was s.c. injected into other nude mice for established a unsort xenograft tumors mode. Tumor growth was monitored thrice a week by calipers to calculate tumor volumes according to the formula (length$\times$width$^2$)/2. The Xenograft tumors tissue was immediately fixed in 10% neutral buffered formalin. The tissues were then embedded in paraffin and sectioned. The sections were stained with hematoxylin and eosin (H&E), and then subjected to histological analysis. Terminal deoxyribo-nucleotidyl transferase-mediated dUTP nick end labeling (TUNEL) staining was done using recombinant terminal transferase (ROCHE, Indianapolis, Ind.) and dUTP-Alexa 594 (MOLECULAR PROBES) according to the instructions of the manufacturers and counterstained by 4',6-diamidino-2-phenylindole. All images were acquired with a Nikon TS800 fluorescence microscope using SPOT camera imaging software.

Cellular Fractionation

Floating and attached cells were harvested from two 60-cm$^2$ dish by centrifugation, resuspended in homogenization buffer (0.25 mol/L sucrose, 10 mmol/L HEPES (pH 7.4), and 1 mmol/L EGTA), and subjected to 40 strokes of homogenization on ice in a 2-mL Dounce homogenizer. The homogenates were centrifuged at 1,000$\times$g at 4° C. for 10 minutes to pellet nuclei. The supernatant was subsequently centrifuged at 14,000$\times$g at 4° C. for 30 minutes to obtain cytosolic (supernatant) fractions.

Western Blotting

Total cell lysates, mitochondrial and cytosolic fractions were purified and separated by 4-20% Tris-Glycine Gel (INVITROGEN, Carlsbad, Calif.) electrophoresis. For active caspase-3, PARP and Hom analysis, total cells were extracted and separated by 4-20% Tris-Glycine Gel (INVITROGEN) electrophoresis. Antibodies used include GFP (Santa Cruz Biotech, Santa Cruz, Calif.), Histone-1 (Ab-1, NEOMARKERS, Fremont, Calif.), and β-actin (SIGMA), active caspase-3 (BD BIOSCIENCES), and PARP (CELL SIGNALING TECHNOLOGY, Boston, Mass.). Appropriate Horseradish peroxidase-conjugated secondary antibodies were used to detect the bound primary antibodies antigen complex and developed with Western Lightning® Western Blot Chemiluminescence Reagent Plus (PERKINELMER, Boston, Mass.).

Reverse Transcription-PCR

Total RNA was isolated using the TRIzol® Reagent (INVITROGEN) according to the instructions of the manufacturer. First-strand cDNA was synthesized using Superscript II reverse transcriptase (INVITROGEN). Subsequently, each RT reaction mixture was subjected to PCR amplification with the number of cycles varying from 20 (GAPDH) to 35 (Hom). Each cycle consisted of a heat denaturation step (94° C. for 60 seconds), an annealing step (57° C. for 30 seconds), and an extension step (72° C. for 30 seconds). The PCR products were size fractionated on a 2% agarose gel, and visualized under ultraviolet light. The primers used to amplify Hom included:

```
                                     (SEQ ID NO: 15)
5'-AAGGCAATTAGGCGCTGCTT-3'
and
                                     (SEQ ID NO: 16)
5'-ACAGAACAACTGAGTCCTCCA-3'.
```

Statistical Analysis

Results are expressed as mean±SD. Statistical analysis was evaluated by ANOVA analysis in which multiple comparisons were performed by using the method of least significant difference. Differences were considered significant if the probability of the difference occurring by chance was <5 in 100 ($P<0.05$).

Results

Hom-1 Encoded a Nuclear Protein

Hom-1 is a human homologue of *Xenopus* Xom and shares similar structure homology. To identify the intracellular localization of Hom-1, an expression vector encoding the full-length Hom-1 protein with an amino-terminal GFP tag was constructed. The constructs were transfected into HCT116 colon cancer cells, and the intracellular distribution of the chimera protein was visualized with confocal microscopy. Nuclei of the HCT116 cells were labeled with PI staining. It was found that Hom-1 was targeted to the nuclei of transfected cells, where it co-localizes with PI. To further verify the nuclear localization of Hom-1, sucrose gradient was used to fraction the sub-subcellular compartments before determining the distribution of Hom-1 in each compartment with Western blot analysis. It was found that Hom-1 was enriched in the nuclear fraction of the transfected cells, while GFP is enriched in the cytoplasmic compartment of the transfected cells.

Hom Suppressed Growth of Human Cancer Cells Through Induction of Apoptosis

As discussed above, Hom-1 is a antagonist of the oncogenic Wnt signaling. To determine the effects of Hom-1 on the growth of solid tumors, assays were carried out to examine the effects of Hom-1 on the growth of human cancer cells.

It was found that HCT116 colon cancer cells, H460 lung cancer cells and a human embryonic kidney cell 293T (transformed with adenovirus E1a and carrying a temperature sensitive T antigen co-selected with neomycin) were transfected with expression vector encoding GFP-Hom-1 or GFP. For all three cell lines, about 35-50% of the cells were transfected as indicated by the GFP signal. Forty-eight hours after transfection, cells growth was analyzed by MTS assay, following manufacture's instruction.

It was found that GFP did not exert any effects on the growth of tested cells. However, GFP-Hom-1 exerted strong inhibition on the growth of tested cancer cells. Interestingly, the growth inhibitory effects of GFP-Hom-1 was minimal non-cancer 293T cell line. These findings is consistent with previous observation named tumor addiction (to oncogenic pathways).

Furthermore, a colony formation assay was conducted to investigate the effect of Hom-1 on long-term cell survival. HCT116 cells were transiently transfected with plasmids encoding GFP-Hom-1 or GFP. Forty-eight hours post-transfection, the cells were collected, and sorted by GFP signal, and then plated in six-well plates at a dilution of $1 \times 10^5$ cells per well. Twenty-four hours post-plating, the HCT116 colon cells (90% attached to plate) were visualized with fluorescent microscopy and phase-contrast microscopy. Ninety-six hours post-plating, the transfected cells were examined again with phase-contrast microscopy and fluorescent microscopy.

It was found that few GFP positive cells were identified in well transfected with GFP-Hom-1 at 96 hours post-plating, suggesting that GFP-Hom-1 suppress the growth of transfected cells. Similar results were also observed in other human cancer cell lines including Sw480, H460 and H1299. Consistent with the results of transient transfection studies, the growth of 293T cell was only slightly inhibited by GFP-Hom-1. Long term growth of the sorted transfected cells showed that multiple colonies formed in GFP-transfected cells, whereas, very few colonies developed in cells transfected with GFP-Hom-1. There was only 20% reduction in the number of colonies in 293T cells transfected with GFP-Hom-1.

To determine whether this growth suppression was as a result of apoptosis in cells transfected with GFP-Hom-1, apoptosis was assessed through microscopic visualization of the transfected cells to determine the presence of apoptotic features, such as condensed chromatin and micronucleation by a Hoechst 33258 staining as previously described (Waldman T, et al. Nature 1996, 381:713). It was found that the GFP did not induce cellular apoptosis, whereas, the GFP-Hom-1 induced significant amount of cellular apoptosis in human cancer cell lines. Moreover, GFP-Hom-1 did not induce apoptosis in 293T cellular, a non-cancer cell line.

These results suggested that Hom-1 is potent inducer of growth suppression in human cancer cells, and the effect is partly through induction of apoptosis. The growth inhibition effects of Hom-1 is significantly less in non-cancer human 293T cells, which may reflect the previous noted phenomena of cancer addiction to oncogenic pathway.

Hom-1 induced apoptotic cells death in p53 deficient cells

P53 is a critical tumor suppressor gene. More than fifty percent of cancers harbor inactive p53 as a result of direct mutations in the p53 gene To determine whether the tumor suppression effect of Hom-1 relays on a functional p53, assays were conducted to investigate the effect of Hom-1 on three cancer cell lines, the HCT116 p53KO, p53 null H1299 and p53 mutated SW480, where the p53 function have been lost either as a result of mutation or artificial knockdown. The methods of analyzing the effects of Hom-1 on the growth of these cancer cells is essentially the same as described above.

MTS assays, in vitro cell growth assays, and colony formation assays were carried out. The results showed that Hom-1 strongly inhibited the growth of these tested cancer cells that lack a functional p53 (P<0.01, respectively). In p53 deficient cells, Hom-1 also induced apoptosis as indicated by apoptotic figures.

Hom-1 Induced Caspase-3 Activation

Caspase-3 is a critical executor of apoptosis. It is either partially or totally responsible for the proteolytic cleavage of many key proteins such as the nuclear enzyme poly (ADP-ribose) polymerase (PARP). Caspase-3 has been identified as a key mediator of apoptosis in mammalian cells. Induction of apoptosis leads to cleavage of procaspase-3 and the generation of an active 17 kDa caspase-3 and 12 kDa caspase-3 fragments. The activate caspase 3 then targets key modulators of the apoptotic pathway including PARP and other caspases.

To investigate whether caspae-3 activation is involved in Hom-mediated apoptosis, total proteins were extracted, and the caspase-3 activation was analyzed by western blotting assay using an active caspase-3 antibody. It was found that expression of GFP-Hom-1 but not GFP activated caspase-3 in both p53 sufficient and deficient cancer cells. These results suggested that Hom-1 induced activation of caspase-3 in a p53 independent manner.

Hom-1 Repressed Tumors Growth by Inducing Apoptotic Cell Death In Vivo

Figure 6A:
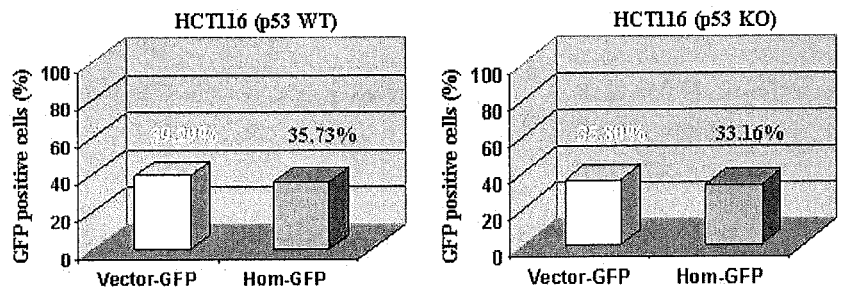
FIGS. 6A-6D are diagrams (FIGS. 6A and 6C) and photographs (FIGS. 6B and 6D) showing: (A) transfection rates of wild type and p53 knockdown HCT116 cells transfected with constructs encoding GFP or GFP-Hom-1 (FIG. 6A); (B) effects of Hom-1 on tumor-bearing nude mice (FIG. 6B) and tumor volumes (FIG. 6C), where tumor growth was significantly repressed in Hom-1-transfected p53 WT and KO cell lines. (Values are mean±SD, n=5 per group, *P<0.01 v.s. vector-transfected cells; (C) apoptosis in xenograft tumors tissue as examined by TUNEL staining (FIG. 6D).
Figure 6B:
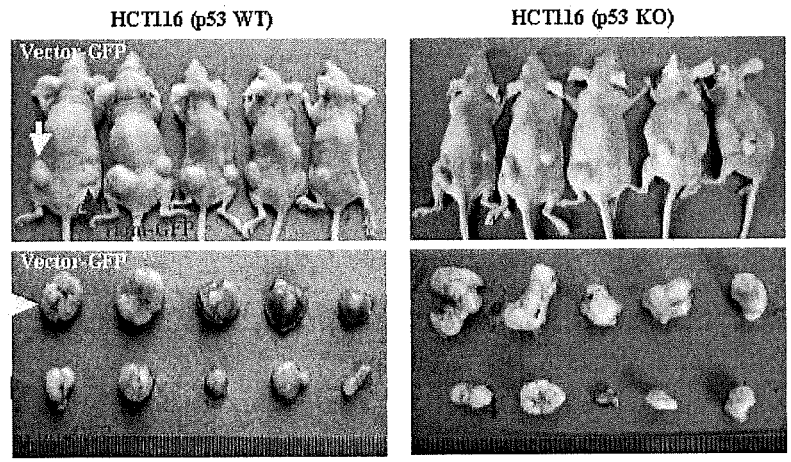
Figure 6C:
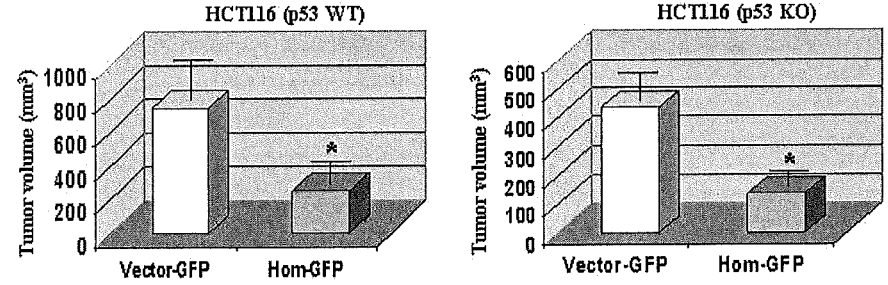
Figure 6D:
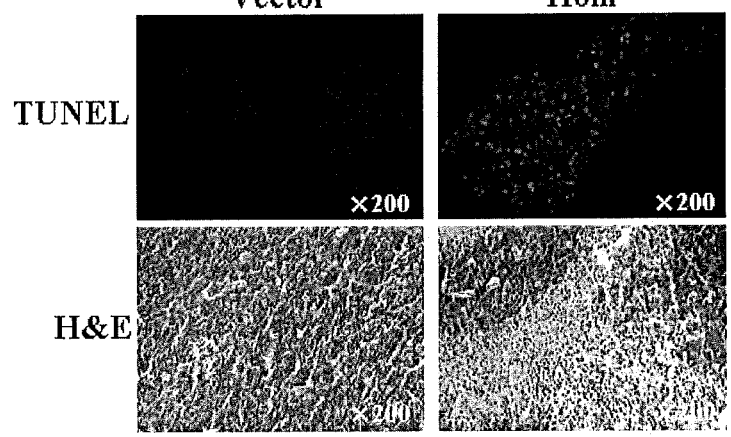

To identify whether Hom-1 confers antitumor activity in vivo, both HCT116 p53 wild-type (WT) cell line and HCT116 p53 knockout (KO) cell line were transfected with expression vectors encoding GFP or GFP-Hom-1. The transfection rate was about 35-40% (FIG. 6A). The growth rates of these transfected cells were determined by injecting the cells subcutaneously in the back of nude mice. The cells expressing GFP were injected into the left side of the back, whereas the cell expressing GFP-Hom-1 were injected into the right side of the back. The growths of the tumors were examined in situ and as excisions (FIG. 6B).

It was found that GFP-Hom-1, but not GFP, repressed the in vivo tumor growth of both p53 sufficient and p53 deficient HCT116 cells. H&E staining and in situ apoptosis analysis by TUNEL staining showed that tumors expressing Hom-1 demonstrated a large number of fragmented DNA, suggesting that Hom-1 repressed tumor growth in vivo by inducing apoptotic cell death.

Example 3: Hom-1 Inhibitor Reduced Expression of Cytokines

Assays were conducted to determine if Hom-1 regulates the expression of proinflammatory cytokines, e.g., interleukin-1 (IL-1), interleukin-6 (IL-6), interleukin-8 (IL-8), tumor necrosis factor-alpha (TNF-alpha), and macrophage colony-stimulating factor (M-CSF), in lymphocytes. Specifically, it was determined whether inhibiting Hom-1 from a cell, via an RNAi agent, would reduce the expression of the cytokines.

Undifferentiated monocyte U937 cells were cultured for four days in media including M-CSF, which induces monocyte differentiation. The cells were electroporated with an RNAi agent directed against either Hom-1 (construct 3) or GFP and then cultured for another three days. It was estimated that only half of the cells electroporated successfully internalized the RNAi agent. Lipopolysaccharide (LPS, 1 µg/ml) was then included in the culture media to initiate cytokine expression; the cells were harvested twenty-four hours later. In the manner described above in Example I, the cells' total RNA was extracted, RT-PCR was performed on the extracted RNA, and real-time PCR quantified the level of IL-1, IL-6, IL-8, or TNF-alpha mRNA in the cells.

It was found that mRNA levels of the cytokines were greatly reduced in the cells electroporated with the RNAi agent against Hom-1. The mRNA level for each of the cytokines was reduced by from 40% to 60% relative to the control cells (i.e., cells electroporated with an RNAi agent against GFP). As about only half of the cells internalized the RNAi agent, the actual magnitudes of the inhibition were greater than 40-60% and should be 100% or close to 100%.

The results suggested that Hom-1 inhibitors, such as RNAi agents, can be used to reduce the expression of proinflammatory cytokines, thereby treating ARDS and other similar respiratory tract/lung disorders that are mediated by these cytokines.

Example 4 Hom-1 Promoted Lymphocyte Development

Hom-1 expression is highly expressed in normal myeloid and lymphoid lineage cells. Its expression is up-regulated during maturation of hematopoietic cells.

Undifferentiated monocyte U937 cells containing either GFP$^{Tet}$ or GFPHom-1$^{Tet}$ were used in these experiments. GFP$^{Tet}$ and GFPHom-1$^{Tet}$ are transgenes that are activated when exposed to tetracycline (Tet) and thereby overexpress GFP and a fusion of GFP and Hom-1, respectively. The cells were cultured in media including Tet for 48 hours. LPS was then added as described-above and the cells were harvested twenty-four hours later. The mRNA levels of IL-1, IL-6, IL-8, TNF-alpha, or M-CSF were determined in the same manner described above.

It was found that the mRNA levels of the cytokines were dramatically increased in cells overexpressing Hom-1. They were about ten to over three-hundred fold greater than the levels in the control cells, which overexpressed only GFP. The results demonstrate that Hom-1 promotes lymphocyte maturation and differentiation.

Further assays were carried out to examine roles of Hom-1 in monocytes and macrophages, which are key players of both innate and adaptive immunity. It was found that Hom-1 plays a pivotal role in monocyte to macrophage differentiation.

More specifically, repressing Hom-1 expression in primary monocytes profoundly impaired terminal macrophage differentiation. Knockdown of Hom-1 expression in monocytes using the above-described siRNA abrogated the morphogenesis of the fibroblast-like shape and substantially diminished the expression of cell surface CD71 marker, FcγRI CD64, CD40, CD86, integrins CD11b and CD11 c, TLR4 (Toll-like receptor 4), MR (mannose receptor), and CD14. Interestingly, the knockdown did not decrease the viability of primary monocytes as determined by trypan blue exclusion. The expression of other cell surface molecules, such as HLA-DR, was not affected by the knockdown of Hom-1, ruling out the possibility that diminished monocyte to macrophage differentiation may result from cytotoxicity of Hom-1 suppression. In addition, monocytes transfected with siRNA exhibited reduced phagocytotic activity compared with the control cells, suggesting that Hom-1 is required for functional development during monocyte to macrophage differentiation Conversely, over-expression of Hom-1 in monocytes accelerated monocyte differentiation into macrophages, as indicated by the elevated expression of CD71 on the surface of transfected cells. Similarly, ectopic expression of Hom-1 in myeloid U937 cells triggered their differentiation with prominent macrophage features, including expression of the above-mentioned markers, pronounced morphology changes (cells became adherent and flattened with extensive pseudopodia), enhanced phagocytotic activity, and increased secretion of pro-inflammatory cytokines. The results further showed that M-CSF receptor is a direct transcriptional target of Hom-1.

The fact that Hom-1 expression correlated positively with the expression of several pro-inflammatory cytokines in clinical patients suggested that Hom-1 plays significant role in pathogenesis and treatment of inflammatory diseases.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting an mRNA or cDNA encoding a Hom-1 polypeptide in a sample, the method comprising:
   performing on an isolated mRNA sample or a cDNA sample generated from the mRNA sample (i) a nucleic acid hybridization assay with an oligonucleotide probe that, under a stringent condition, hybridizes to a reference nucleic acid, or (ii) a nucleic acid amplification assay with a pair of primers for amplifying the reference nucleic acid or a fragment thereof, and
   detecting hybridization of the probe to an mRNA or cDNA molecule or an amplified nucleic acid molecule flanked by the pair of primers, whereby an mRNA or cDNA encoding a Hom-1 polypeptide is detected if the hybridization or the amplified nucleic acid molecule is detected,
wherein the reference nucleic acid consists of the sequence of SEQ ID NO:3 or the complement thereof, the reference nucleic acid being a 5' untranslated region in the mRNA or cDNA encoding the Hom-1 polypeptide.

2. The method of claim 1, wherein the sample is a bodily fluid, tissue, or cell sample.

3. The method of claim 1, wherein the hybridization assay is a Southern blot, Northern blot, or in situ hybridization.

4. The method of claim 1, wherein the amplification assay is polymerase chain reaction (PCR), reverse transcription PCR, quantitative PCR, or in situ PCR.

5. The method of claim 4, wherein reverse transcription PCR is performed.

6. The method of claim 4, wherein quantitative PCR is performed.

7. The method of claim 1, wherein the sample is from a subject having or suspected of having a cellular proliferative disorder.

8. The method of claim 1, wherein the sample is from a subject having or suspected of having an immune disorder.

9. The method of claim 1, wherein the Hom-1 polypeptide contains the sequence of SEQ ID NO:1.

* * * * *